US010626393B2

(12) United States Patent
Lee et al.

(10) Patent No.: US 10,626,393 B2
(45) Date of Patent: Apr. 21, 2020

(54) DELIVERING CRISPR THERAPEUTICS WITH LIPID NANOPARTICLES

(71) Applicant: ARBUTUS BIOPHARMA CORPORATION, Burnaby (CA)

(72) Inventors: Amy C. H. Lee, Burnaby (CA); Nicholas D. Weber, Burnaby (CA)

(73) Assignee: ARBUTUS BIOPHARMA CORPORATION, Burnaby, BC (CA)

( * ) Notice: Subject to any disclaimer, the term of this patent is extended or adjusted under 35 U.S.C. 154(b) by 3 days.

(21) Appl. No.: 15/570,103

(22) PCT Filed: Jun. 6, 2016

(86) PCT No.: PCT/US2016/036069
§ 371 (c)(1),
(2) Date: Oct. 27, 2017

(87) PCT Pub. No.: WO2016/197133
PCT Pub. Date: Dec. 8, 2016

(65) Prior Publication Data
US 2018/0148719 A1    May 31, 2018

Related U.S. Application Data

(60) Provisional application No. 62/171,148, filed on Jun. 4, 2015.

(51) Int. Cl.
| | |
|---|---|
| *C12N 15/113* | (2010.01) |
| *A61K 48/00* | (2006.01) |
| *A61K 9/51* | (2006.01) |
| *C07K 7/06* | (2006.01) |
| *C12N 9/22* | (2006.01) |
| *C12N 15/11* | (2006.01) |
| *A61K 9/127* | (2006.01) |

(52) U.S. Cl.
CPC ............ *C12N 15/113* (2013.01); *A61K 9/127* (2013.01); *A61K 9/5123* (2013.01); *A61K 9/5146* (2013.01); *A61K 48/0025* (2013.01); *C07K 7/06* (2013.01); *C12N 9/22* (2013.01); *C12N 15/111* (2013.01); *C12N 15/1131* (2013.01); *C12N 15/1137* (2013.01); *C12N 2310/10* (2013.01); *C12N 2310/20* (2017.05); *C12N 2310/3513* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | |
|---|---|---|
| 9,254,265 B2 | 2/2016 | Geall et al. |
| 2013/0259924 A1 | 10/2013 | Bancel et al. |
| 2015/0232883 A1 | 8/2015 | Dahlman et al. |

FOREIGN PATENT DOCUMENTS

| | | |
|---|---|---|
| EP | 2966170 A1 | 1/2016 |
| WO | 2013151665 A2 | 10/2013 |
| WO | 2014089486 A1 | 6/2014 |
| WO | 2014204726 A1 | 12/2014 |
| WO | 2015006498 A2 | 1/2015 |
| WO | 2015006747 A2 | 1/2015 |
| WO | 2015011633 A1 | 1/2015 |
| WO | 2015089465 A1 | 6/2015 |
| WO | 2015126927 A2 | 8/2015 |
| WO | 2016197132 A1 | 12/2016 |

OTHER PUBLICATIONS

Amelio, et al., "CRISPR: a new method for genetic engineering—A prokaryotic immune component may potentially open a new era of gene silencing", Cell Death and Differentiation 22, 3-5 (2015).
Ding, et al., "Use of a CRISPR/Cas System for Cardiovascular Disease Modeling and Therapeutic Applications", Circulation, Abstract 18593, vol. 128, 18593 (2013).
Dong, et al., "Targeting Hepatitis B Virus cccDNA by CRISPR/Cas9 Nuclease Efficiently Inhibits Viral Replication", Antiviral Research 118, 110-117 (2015).
Lin, et al., "The CRISPR/Cas9 System Facilitates Clearance of the Intrahepatic HBV Templates In Vivo", Molecular Therapy-Nucleic Acids 3, e186, 7 pages (2014).
Liu, et al., "Cationic lipid-mediated delivery of proteins enables efficient protein-based genome editing in vitro and in vivo", Nature Biotechnology Advanced Online Publication, 10 pages (2014).
Maclachlan, et al., "Recent Advances in the Lipid Nanoparticle-Mediated Delivery of Messenger RNA", AsiaTIDES Conference, 19 pages (Feb. 25, 2014).
Mali, et al., "C as9 as a versatile tool for engineering biology", Nature Methods 10(10), 957-963 (2013).
Patent Cooperation Treaty, International Searching Authority, Search Report and Written Opinion for PCT/US2016/036069, 16 pages, dated Oct. 7, 2016.
Ramanan, et al., "CRISPR/Cas9 Cleavage of Viral DNA Efficiently Suppresses Hepatitis B Virus", Scientific Reports 5, 10833, 9 pages (2015).
Ramanan, et al., "CRISPR/Cas9 Cleavage of Viral DNA Efficiently Suppresses Hepatitis B Virus", Scientific Reports, 1-10 (2015).
Ran, et al., "In vivo genome editing using *Staphylococcus aureus* Cas9", Nature 520(7546), 186-191, Supp Information 1-33 (2015).
Sander, et al., "CRISPR-Cas systems for editing, regulating and targeting genomes", Nature Biotechnol 32(4), 347-355, Supp Material, 4 pages (2014).
Seeger, et al., "Targeting Hepatitis B Virus With CRISPIR/Cas9", Citation: Molecular Therapy—Nucleic Acids 3, e216 (2014).

(Continued)

*Primary Examiner* — Robert M Kelly
(74) *Attorney, Agent, or Firm* — Viksnins Harris Padys Malen LLP

(57) ABSTRACT

The present invention provides lipid particles comprising therapeutic nucleic acids such as gRNA that target gene expression.

15 Claims, No Drawings
Specification includes a Sequence Listing.

(56) References Cited

OTHER PUBLICATIONS

Wiedenheft, et al., "RNA-guided genetic silencing systems in bacteria and archaea", Nature 482, 331-338 (2012).
Zhen, et al., "Harnessing the Clustered Regularly Interspaced Short Palindrome Repeat (CRISPR)/CRISPR-associated Cas9 System to Distrupt the Hepatitis B Virus", Gene Therapy 22(5), 404-412 (2015).

DELIVERING CRISPR THERAPEUTICS WITH LIPID NANOPARTICLES

CROSS-REFERENCE TO RELATED APPLICATION(S)

This patent application claims the benefit of priority of U.S. application Ser. No. 62/171,148, filed Jun. 4, 2015, which application is herein incorporated by reference.

SEQUENCE LISTING

The instant application contains a Sequence Listing which has been submitted in ASCII format via EFS-Web and is hereby incorporated by reference in its entirety. Said ASCII copy, created on May 16, 2018, is named 08155_043US1_SL.txt and is 8,192 bytes in size.

BACKGROUND

Targeted genome editing using engineered nucleases has progressed from being a niche technology to a method used by many biological researchers. This adoption has been largely fueled by the emergence of the clustered, regularly interspaced, short palindromic repeat (CRISPR) technology, an important new approach for generating RNA-guided nucleases, such as Cas9. See, e.g., Sander et al., *Nature Biotechnology*, 32(4), 347-355, including Supplementary Information (2014).

There is a continuing need for compositions and methods for delivering CRISPR therapeutics to patients in need thereof.

BRIEF SUMMARY

Provided herein are compositions and methods for utilizing CRISPR technology to treat disease by using lipid nanoparticles to deliver CRISPR therapeutics. The methods of the invention are useful, for example, for the treatment of a targeted disease when administered in a therapeutic amount to a human subject having the disease. More generally, the invention provides lipid nanoparticles that are capable of inhibiting or silencing target gene expression in vitro and in vivo by delivering CRISPR therapeutics.

The present invention provides nucleic acid-lipid particles, and formulations thereof, wherein the lipid particles each include one or more (e.g., a cocktail) of the molecules described herein, a cationic lipid, and a non-cationic lipid, and optionally a conjugated lipid that inhibits aggregation of particles.

The present invention also provides formulations that include gRNA encapsulated within lipid particles. The different gRNA molecules may be co-encapsulated in the same lipid particle, or each type of gRNA species present in the cocktail may be encapsulated in separate particles, or some gRNA species may be coencapsulated in the same particle while other gRNA species are encapsulated in different particles within the formulation. Typically, the gRNA molecules of the invention are fully encapsulated in the lipid particle. In certain embodiments, the lipid particles comprise both gRNA and an mRNA encoding a Cas9. In certain embodiments, one population lipid particles comprises the gRNA and another population of lipid particles comprises the mRNA encoding a Cas9, which lipid particles may be in the same composition or in different compositions, and may be administered concurrently or sequentially.

The nucleic acid-lipid particles of the invention are useful for the prophylactic or therapeutic delivery, into a human having a disease, of gRNA molecules that silence the expression of one or more genes associated with the disease, thereby ameliorating at least one symptom of the disease in the human. In some embodiments, one or more of the gRNA molecules described herein are formulated into nucleic acid-lipid particles, and the particles are administered to a mammal (e.g., a human) requiring such treatment. In certain instances, a therapeutically effective amount of the nucleic acid-lipid particle can be administered to the mammal. Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particle is administered systemically, e.g., via enteral or parenteral routes of administration.

In some embodiments, downregulation of target gene expression is determined by detecting target RNA or protein levels in a biological sample from a mammal after nucleic acid-lipid particle administration. In other embodiments, downregulation of target gene expression is determined by detecting target mRNA or protein levels in a biological sample from a mammal after nucleic acid-lipid particle administration. In certain embodiments, downregulation of target gene expression is detected by monitoring symptoms associated with target infection in a mammal after particle administration. In certain embodiments, inactivating mutations (e.g., specific inactivating mutations) in target DNA are detected to determine the efficacy of CRISPR/Cas9 at inactivating target expression.

In another embodiment, the present invention provides methods for introducing a combination of gRNA and Cas9 to silence target gene expression in a living cell, the method comprising the step of contacting the cell with a nucleic acid-lipid particle of the invention, wherein the nucleic acid-lipid particle includes an gRNA that targets target, under conditions whereby the gRNA enters the cell with the Cas9 mRNA and silences the expression of a target gene within the cell.

In another embodiment, the present invention provides methods for silencing target gene expression in a mammal (e.g., a human) in need thereof, wherein the methods each include the step of administering to the mammal a nucleic acid-lipid particle of the present invention.

In a further aspect, the present invention provides for use of a pharmaceutical composition of the present invention for inhibiting target gene expression in a living cell.

The compositions of the invention are also useful, for example, in biological assays (e.g., in vivo or in vitro assays) for inhibiting the expression of one or more target genes.

Other objects, features, and advantages of the present invention will be apparent to one of skill in the art from the following.

DETAILED DESCRIPTION

The therapy described herein advantageously provides significant new compositions and methods for treating targeted disease(s) in human beings and the symptoms associated therewith. Embodiments of the present invention can be administered, for example, once per day, once per week, or once every several weeks (e.g., once every two, three, four, five or six weeks).

Furthermore, the nucleic acid-lipid particles described herein enable the effective delivery of a nucleic acid drug into target tissues and cells within the body. The presence of the lipid particle confers protection from nuclease degradation in the bloodstream, allows preferential accumulation in target tissue and provides a means of drug entry into the cells.

Accordingly, certain embodiments of the present invention provide a nucleic acid-lipid particle comprising: (a) one or more guide RNA (gRNA) sequences that comprise a first sequence that corresponds to a target sequence and a second sequence that is a tracer RNA sequence, e.g., located 3' of the first sequence; (b) a cationic lipid; and (c) a non-cationic lipid.

In certain embodiments, the nucleic acid-lipid particle further comprises a mRNA sequence encoding a CRISPR associated protein 9 (Cas9).

In certain embodiments, the mRNA sequence encoding the Cas9 further comprises a sequence encoding a nuclear localization signal (NLS).

In certain embodiments, the NLS is a PKKKRKV (SEQ ID NO:1).

In certain embodiments, the mRNA sequence encoding the Cas9 further comprises a polyA tail, a 5' untranslated region (UTR) and/or a 3' UTR.

In certain embodiments, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA; Compound (15)), 3-((6Z,9Z,28Z,31Z)-heptatriaconta-6,9,28,31-tetraen-9-yloxy)-N,N-dimethylpropan-1-amine (DLin-MP-DMA; Compound (8)), (6Z,9Z,28Z,31Z)-heptatriaconta-6,9,28,31-tetraen-19-yl 4-(dimethylamino)butanoate) (Compound (7)), (6Z,16Z)-12-((Z)-dec-4-enyl)docosa-6,16-dien-11-yl 5-(dimethylamino)pentanoate (Compound (13)), a salt thereof, and a mixture thereof.

In certain embodiments, the non-cationic lipid is cholesterol or a derivative thereof.

In certain embodiments, the non-cationic lipid is a phospholipid.

In certain embodiments, the nucleic acid-lipid particle further comprises a conjugated lipid that inhibits aggregation of particles.

In certain embodiments, the conjugated lipid that inhibits aggregation of particles is a polyethyleneglycol (PEG)-lipid conjugate.

In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof.

In certain embodiments, the PEG-lipid conjugate is a PEG-DAA conjugate.

In certain embodiments, the PEG-DAA conjugate is selected from the group consisting of a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

In certain embodiments, the gRNA is fully encapsulated in the particle.

In certain embodiments, the particle has a total lipid:gRNA mass ratio of from about 5:1 to about 15:1.

In certain embodiments, the particle has a median diameter of from about 30 nm to about 150 nm.

In certain embodiments, the particle has an electron dense core.

In certain embodiments, the cationic lipid comprises from about 48 mol % to about 62 mol % of the total lipid present in the particle.

In certain embodiments, the nucleic acid-lipid particle comprises a phospholipid and cholesterol or cholesterol derivative, wherein the phospholipid comprises from about 7 mol % to about 17 mol % of the total lipid present in the particle and the cholesterol or derivative thereof comprises from about 25 mol % to about 40 mol % of the total lipid present in the particle.

In certain embodiments, the conjugated lipid that inhibits aggregation of particles comprises from about 0.5 mol % to about 3 mol % of the total lipid present in the particle.

In certain embodiments, the lipids are formulated as described in any one of formulations A, B, C, D, E, F, G, H, I, J, K, L, M, N, O, P, Q, R, S, T, U, V, W, X, Y or Z.

In certain embodiments, the nucleic acid-lipid particle comprises two different gRNA sequences.

In certain embodiments, the nucleic acid-lipid particle comprises three different gRNA sequences.

In certain embodiments, the nucleic acid-lipid particle comprises four different gRNA sequences.

In certain embodiments, the nucleic acid-lipid particle comprises five different gRNA sequences.

In certain embodiments, the target sequence corresponds to a target sequence described in International Publication Number WO 2013/151665.

Certain embodiments provide a pharmaceutical composition comprising a nucleic acid-lipid particle described herein and a pharmaceutically acceptable carrier.

Certain embodiments provide a pharmaceutical composition comprising a nucleic acid-lipid particle as described herein and a pharmaceutically acceptable carrier, which composition optionally comprises a second nucleic acid-lipid particle comprising a mRNA sequence encoding a Cas9, which second nucleic acid-lipid particle does not comprise a gRNA.

Certain embodiments provide a method for silencing expression of a target gene in a cell, the method comprising the step of contacting a cell comprising an expressed target gene with a composition described herein under conditions to silence the expression of the gene within the cell.

In certain embodiments, the cell is in a mammal.

In certain embodiments, the cell is contacted by administering the particle to the mammal via a systemic route.

Certain embodiments provide a nucleic acid-lipid particle or a pharmaceutical composition described herein for use in silencing expression of a gene (e.g., a target gene) in a cell in a mammal (e.g., a human).

Certain embodiments provide the use of a nucleic acid-lipid particle or a pharmaceutical composition described herein to prepare a medicament for silencing expression of a gene (e.g., a target gene) in a cell in a mammal (e.g., a human).

As used herein, the following terms have the meanings ascribed to them unless specified otherwise.

Briefly, the CRISPR technology can be utilized by combining the CRISPR associated protein 9 (Cas9), an RNA-guided DNA endonuclease enzyme, with a guide RNA (gRNA) sequence that is designed to be utilized by the Cas9 to target a specific sequence. This combination functions to inhibit target gene expression.

An example of an open reading frame (ORF) for the *Streptococcus pyogenes* (SP) Cas9, found in a plasmid provided by the George Church Lab to addgene.org, is provided below. The mRNA encoding Cas9 will also generally include a polyA tail and other elements (e.g., including 5' & 3' UTR). Cas9 mRNA can also be purchased, e.g., from TriLink BioTechnologies, Inc. Other versions of this Cas9 mRNA may be used by varying the codons without changing the translated protein. Also the nature of the NLS (nuclear localization signal) can vary. An example includes a SV40 NLS (PKKKRKV; SEQ ID NO:1) at the 3' end. Further descriptions of CRISPR related proteins, and the expression thereof, can be found, e.g., in International Publication Number WO 2015/006747.

An Open Reading Frame for the *Streptococcus pyogenes* (SP) Cas9 (SEQ ID NO:2)

5'ATGGACAAGAAGTACTCCATTGGGCTCGATATCGGCACAAACAGCGT

CGGCTGGGCCGTCATTACGGACGAGTACAAGGTGCCGAGCAAAAATTC

AAAGTTCTGGGCAATACCGATCGCCACAGCATAAAGAAGAACCTCATTG

GCGCCCTCCTGTTCGACTCCGGGGAGACGGCCGAAGCCACGCGGCTCAA

AAGAACAGCACGGCGCAGATATACCCGCAGAAAGAATCGGATCTGCTAC

CTGCAGGAGATCTTTAGTAATGAGATGGCTAAGGTGGATGACTCTTTCT

TCCATAGGCTGGAGGAGTCCTTTTTGGTGGAGGAGGATAAAAAGCACGA

GCGCCACCCAATCTTTGGCAATATCGTGGACGAGGTGGCGTACCATGAA

AAGTACCCAACCATATATCATCTGAGGAAGAAGCTTGTAGACAGTACTG

ATAAGGCTGACTTGCGGTTGATCTATCTCGCGCTGGCGCATATGATCAA

ATTTCGGGGACACTTCCTCATCGAGGGGGACCTGAACCCAGACAACAGC

GATGTCGACAAACTCTTTATCCAACTGGTTCAGACTTACAATCAGCTTT

TCGAAGAGAACCCGATCAACGCATCCGGAGTTGACGCCAAAGCAATCCT

GAGCGCTAGGCTGTCCAAATCCCGGCGGCTCGAAAACCTCATCGCACAG

CTCCCTGGGGAGAAGAAGAACGGCCTGTTTGGTAATCTTATCGCCCTGT

CACTCGGGCTGACCCCCAACTTTAAATCTAACTTCGACCTGGCCGAAGA

TGCCAAGCTTCAACTGAGCAAAGACACCTACGATGATGATCTCGACAAT

CTGCTGGCCCAGATCGGCGACCAGTACGCAGACCTTTTTTGGCGGCAA

AGAACCTGTCAGACGCCATTCTGCTGAGTGATATTCTGCGAGTGAACAC

GGAGATCACCAAAGCTCCGCTGAGCGCTAGTATGATCAAGCGCTATGAT

GAGCACCACCAAGACTTGACTTTGCTGAAGGCCCTTGTCAGACAGCAAC

TGCCTGAGAAGTACAAGGAAATTTTCTTCGATCAGTCTAAAAATGGCTA

CGCCGGATACATTGACGGCGGAGCAAGCCAGGAGGAATTTTACAAATTT

ATTAAGCCCATCTTGGAAAAATGGACGGCACCGAGGAGCTGCTGGTAAA

GCTTAACAGAGAAGATCTGTTGCGCAAACAGCGCACTTTCGACAATGGA

AGCATCCCCCACCAGATTCACCTGGGCGAACTGCACGCTATCCTCAGGC

GGCAAGAGGATTTCTACCCCTTTTTGAAAGATAACAGGGAAAAGATTGA

GAAAATCCTCACATTTCGGATACCCTACTATGTAGGCCCCCTCGCCCGG

GGAAATTCCAGATTCGCGTGGATGACTCGCAAATCAGAAGAGACCATCA

CTCCCTGGAACTTCGAGGAAGTCGTGGATAAGGGGGCCTCTGCCCAGTC

CTTCATCGAAAGGATGACTAACTTTGATAAAAATCTGCCTAACGAAAAG

GTGCTTCCTAAACACTCTCTGCTGTACGAGTACTTCACAGTTTATAACG

AGCTCACCAAGGTCAAATACGTCACAGAAGGGATGAGAAAGCCAGCATT

CCTGTCTGGAGAGCAGAAGAAAGCTATCGTGGACCTCCTCTTCAAGACG

AACCGGAAAGTTACCGTGAAACAGCTCAAAGAAGACTATTTCAAAAAGA

TTGAATGTTTCGACTCTGTTGAAATCAGCGGAGTGGAGGATCGCTTCAA

CGCATCCCTGGGAACGTATCACGATCTCCTGAAAATCATTAAAGACAAG

GACTTCCTGGACAATGAGGAGAACGAGGACATTCTTGAGGACATTGTCC

TCACCCTTACGTTGTTTGAAGATAGGGAGATGATTGAAGAACGCTTGAA

AACTTACGCTCATCTCTTCGACGACAAAGTCATGAAACAGCTCAAGAGG

CGCCGATATACAGGATGGGGCGGCTGTCAAGAAAACTGATCAATGGGA

TCCGAGACAAGCAGAGTGGAAAGACAATCCTGATTTTCTTAAGTCCGAT

GGATTTGCCAACCGGAACTTCATGCAGTTGATCCATGATGACTCTCTCA

CCTTTAAGGAGGACATCCAGAAAGCACAAGTTTCTGGCCAGGGGACAG

TCTTCACGAGCACATCGCTAATCTTGCAGGTAGCCCAGCTATCAAAAAG

GGAATACTGCAGACCGTTAAGGTCGTGGATGAACTCGTCAAAGTAATGG

GAAGGCATAAGCCCGAGAATATCGTTATCGAGATGGCCCGAGAGAACCA

AACTACCCAGAAGGGACAGAAGAACAGTAGGGAAAGGATGAAGAGGATT

GAAGAGGGTATAAAAGAACTGGGGTCCCAAATCCTTAAGGAACACCCAG

TTGAAAACACCCAGCTTCAGAATGAGAAGCTCTACCTGTACTACCTGCA

GAACGGCAGGGACATGTACGTGGATCAGGAACTGGACATCAATCGGCTC

TCCGACTACGACGTGGATCATATCGTGCCCCAGTCTTTTCTCAAAGATG

ATTCTATTGATAATAAAGTGTTGACAAGATCCGATAAAAATAGAGGGAA

GAGTGATAACGTCCCCTCAGAAGAAGTTGTCAAGAAAATGAAAAATTAT

TGGCGGCAGCTGCTGAACGCCAAACTGATCACACAACGGAAGTTCGATA

ATCTGACTAAGGCTGAACGAGGTGGCCTGTCTGAGTTGGATAAAGCCGG

CTTCATCAAAAGGCAGCTTGTTGAGACACGCCAGATCACCAAGCACGTG

GCCCAAATTCTCGATTCACGCATGAACACCAAGTACGATGAAAATGACA

AACTGATTCGAGAGGTGAAAGTTATTACTCTGAAGTCTAAGCTGGTCTC

AGATTTCAGAAAGGACTTTCAGTTTTATAAGGTGAGAGAGATCAACAAT

TACCACCATGCGCATGATGCCTACCTGAATGCAGTGGTAGGCACTGCAC

TTATCAAAAAATATCCCAAGCTTGAATCTGAATTTGTTTACGGAGACTA

TAAAGTGTACGATGTTAGGAAAATGATCGCAAAGTCTGAGCAGGAAATA

GGCAAGGCCACCGCTAAGTACTTCTTTTACAGCAATATTATGAATTTTT

TCAAGACCGAGATTACACTGGCCAATGGAGAGATTCGGAAGCGACCACT

TATCGAAACAAACGGAGAAACAGGAGAAATCGTGTGGGACAAGGGTAGG

GATTTCGCGACAGTCCGGAAGGTCCTGTCCATGCCGCAGGTGAACATCG

TTAAAAAGACCGAAGTACAGACCGGAGGCTTCTCCAAGGAAAGTATCCT

CCCGAAAAGGAACAGCGACAAGCTGATCGCACGCAAAAAAGATTGGGAC

CCCAAGAAATACGGCGGATTCGATTCTCCTACAGTCGCTTACAGTGTAC

TGGTTGTGGCCAAAGTGGGAAAGGGAAGTCTAAAAAACTCAAAAGCGTC

AAGGAACTGCTGGGCATCACAATCATGGAGCGATCAAGCTTCGAAAAA

ACCCCATCGACTTTCTCGAGGCGAAAGGATATAAAGAGGTCAAAAAGA

CCTCATCATTAAGCTTCCCAAGTACTCTCTCTTTGAGCTTGAAAACGGC

-continued

CGGAAACGAATGCTCGCTAGTGCGGGCGAGCTGCAGAAAGGTAACGAGC

TGGCACTGCCCTCTAAATACGTTAATTTCTTGTATCTGGCCAGCCACTA

TGAAAAGCTCAAAGGGTCTCCCGAAGATAATGAGCAGAAGCAGCTGTTC

GTGGAACAACACAAACACTACCTTGATGAGATCATCGAGCAAATAAGCG

AATTCTCCAAAAGAGTGATCCTCGCCGACGCTAACCTCGATAAGGTGCT

TTCTGCTTACAATAAGCACAGGGATAAGCCCATCAGGGAGCAGGCAGAA

AACATTATCCACTTGTTTACTCTGACCAACTTGGGCGCGCCTGCAGCCT

TCAAGTACTTCGACACCACCATAGACAGAAAGCGGTACACCTCTACAA

GGAGGTCCTGGACGCCACACTGATTCATCAGTCAATTACGGGGCTCTAT

GAAACAAGAATCGACCTCTCTCAGCTCGGTGGAGACAGCAGGGCTGACC

CCAAGAAGAAGAGGAAGGTGTGA3'

CRISPR Guide RNA (gRNA)

Regarding gRNA described herein, the first 20 Ns in gRNA sequence below correspond to a target sequence. The remaining portion of the gRNA sequence (the tracer RNA sequence) comprises sequences for guiding the gRNA into the Cas9. The gRNA scaffold below was described in Sander et al., *Nature Biotechnology*, 32(4), 347-355, including Supplementary Information (2014). As is described in Sander et al., different gRNA strategies (e.g., utilizing different tracer RNA sequences) have been tried with more or less success.

AgRNASequence
                                        (SEQ ID NO: 3)
5'*NNNNNNNNNNNNNNNNNNNN*GUUUUAGAGCUAGAAAUAGCAAGUUAAA
AUAAGGCUAGUCCGUUAUCAACUUGAAAAAGUGGCACCGAGUCGGUGCUU
UU3'

Other examples of tracer RNA sequences are provided below. (see, e.g., Ran et al., Nature, 520, 186-191 (2015))

A Tracer RNA for *Streptococcus aureus* (SA)
                                        (SEQ ID NO: 4)
5'GUUUUAGUACUCUGGAAACAGAAUCUACUAAAACAAGGCAAAAUGCCG
UGUUUAUCUCGUCAACUUGUUGGCGAGAUUUU3'

A Tracer RNA for *Streptococcus thermophilus* (ST)
                                        (SEQ ID NO: 5)
5'GUUUUUGUACUCGAAAGAAGCUACAAAGAUAAGGCUUCAUGCCGAAAU
CAACACCCUGUCAUUUUAUGGCAGGGUGUUUU3'

The tracer RNA sequence of the gRNA of the present invention in certain embodiments corresponds to one of the three tracer sequences described hereinabove. In certain embodiments, the tracer sequence is at least 90% identical to any one of the three tracer sequences (e.g., at least 90%, 91%, 92%, 93%, 94%, 95%, 96%, 97%, 98% or 99% identical).

International Publication Number WO 2013/151665 (e.g., see Table 6; which document is specifically incorporated by reference, particularly including Table 6, and the associated Sequence Listing) describes about 35,000 mRNA sequences, claimed in the context of an mRNA expression construct. Certain embodiments of the present invention provide lipid nanoparticles that comprise CRISPR components that target the expression of any of these sequences.

Cas9 recognizes protospacer adjacent motifs (PAMs) in nucleic acid sequences. As such, in certain embodiments, the target sequences are associated with a PAM sequence, such as a PAM sequence in the chart below.

| Species | PAM Sequence |
| --- | --- |
| *Streptococcus pyogenes* (SP) | NGG |
| *Neisseria meningitidis* (NM) | NNNNGATT |
| *Streptococcus thermophilus* (ST) | NNAGAAW |
| *Streptococcus aureus* (SA) | NNGRRT |

The phrase "inhibiting expression of a target gene" refers to the ability to silence, reduce, or inhibit expression of a target gene. To examine the extent of gene silencing, a test sample (e.g., a biological sample from an organism of interest expressing the target gene or a sample of cells in culture expressing the target gene) is contacted with a composition that silences, reduces, or inhibits expression of the target gene. Expression of the target gene in the test sample is compared to expression of the target gene in a control sample (e.g., a biological sample from an organism of interest expressing the target gene or a sample of cells in culture expressing the target gene) that is not contacted with the composition. Control samples (e.g., samples expressing the target gene) may be assigned a value of 100%. In particular embodiments, silencing, inhibition, or reduction of expression of a target gene is achieved when the value of the test sample relative to the control sample (e.g., buffer only, an gRNA sequence that targets a different gene, a scrambled gRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art. An "effective amount" or "therapeutically effective amount" of a therapeutic nucleic acid is an amount sufficient to produce the desired effect, e.g., an inhibition of expression of a target sequence in comparison to the normal expression level detected in the absence of the nucleic acid. In particular embodiments, inhibition of expression of a target gene or target sequence is achieved when the value obtained relative to the control (e.g., buffer only, an gRNA sequence that targets a different gene, a scrambled gRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays for measuring the expression of a target gene or target sequence include, but are not limited to, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "nucleic acid" as used herein refers to a polymer containing at least two nucleotides (i.e., deoxyribonucleotides or ribonucleotides) in either single- or double-stranded form and includes DNA and RNA. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphoramidates, methyl phosphonates, chiral-methyl phosphonates, 2'-O-methyl ribonucleotides, and peptide-nucleic acids (PNAs).

The term "nucleic acid" includes any oligonucleotide or polynucleotide, with fragments containing up to 60 nucleotides generally termed oligonucleotides, and longer fragments termed polynucleotides. A deoxyribooligonucleotide consists of a 5-carbon sugar called deoxyribose joined covalently to phosphate at the 5' and 3' carbons of this sugar to form an alternating, unbranched polymer. DNA may be in the form of, e.g., antisense molecules, plasmid DNA, pre-condensed DNA, a PCR product, vectors, expression cassettes, chimeric sequences, chromosomal DNA, or derivatives and combinations of these groups. A ribooligonucleotide consists of a similar repeating structure where the 5-carbon sugar is ribose. Accordingly, in the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260: 2605-2608 (1985); Rossolini et al., *Mol. Cell. Probes*, 8:91-98 (1994)).

In certain embodiments, a nucleic acid sequence may include at least one "unlocked nucleobase analogue" (UNA).

The invention encompasses isolated or substantially purified nucleic acid molecules and compositions containing those molecules. In the context of the present invention, an "isolated" or "purified" DNA molecule or RNA molecule is a DNA molecule or RNA molecule that exists apart from its native environment. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "unlocked nucleobase analogue" (abbreviated as "UNA") refers to an acyclic nucleobase in which the C2' and C3' atoms of the ribose ring are not covalently linked. The term "unlocked nucleobase analogue" includes nucleobase analogues having the following structure identified as Structure A:

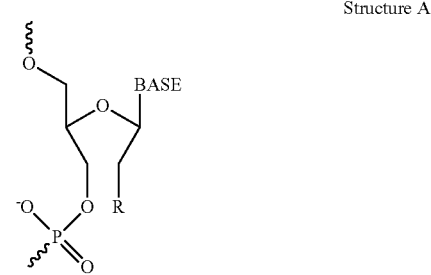

Structure A wherein R is hydroxyl, and Base is any natural or unnatural base such as, for example, adenine (A), cytosine (C), guanine (G) and thymine (T). UNA useful in the practice of the present invention include the molecules identified as acyclic 2'-3'-seco-nucleotide monomers in U.S. Pat. No. 8,314,227 which is incorporated by reference herein in its entirety.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., gRNA) to a target site of interest (e.g., cell, tissue, organ, and the like). In preferred embodiments, the lipid particle of the invention is typically formed from a cationic lipid, a non-cationic lipid, and optionally a conjugated lipid that prevents aggregation of the particle. A lipid particle that includes a nucleic acid molecule (e.g., gRNA molecule) is referred to as a nucleic acid-lipid particle. Typically, the nucleic acid is fully encapsulated within the lipid particle, thereby protecting the nucleic acid from enzymatic degradation.

In certain instances, nucleic acid-lipid particles are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a lipid particle as set forth in PCT Publication No. WO 00/03683, the disclosure of which is herein incorporated by reference in its entirety for all purposes.

The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid such as a gRNA, with full encapsulation, partial encapsulation, or both. In a preferred embodiment, the nucleic acid (e.g., gRNA) is fully encapsulated in the lipid particle (e.g., to form a nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, γ-DLen-C2K-DMA, DLin-M-C2-DMA (also known as MC2), and DLin-M-C3-DMA (also known as MC3).

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (=O), two hydrogen atoms are replaced. In this regard, substituents include, but are not limited to, oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$. The term "optionally substituted," when used before a list of substituents, means that each of the substituents in the list may be optionally substituted as described herein.

The term "halogen" includes fluoro, chloro, bromo, and iodo.

The term "fusogenic" refers to the ability of a lipid particle to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

The term "electron dense core", when used to describe a lipid particle of the present invention, refers to the dark appearance of the interior portion of a lipid particle when visualized using cryo transmission electron microscopy ("cyroTEM"). Some lipid particles of the present invention have an electron dense core and lack a lipid bilayer structure. Some lipid particles of the present invention have an electron dense core, lack a lipid bilayer structure, and have an inverse Hexagonal or Cubic phase structure. While not wishing to be bound by theory, it is thought that the non-bilayer lipid packing provides a 3-dimensional network of lipid cylinders with water and nucleic acid on the inside, i.e., essentially a lipid droplet interpenetrated with aqueous channels containing the nucleic acid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the liver, heart, pancreas, kidney, and the like.

The term "virus particle load", as used herein, refers to a measure of the number of virus particles present in a bodily fluid, such as blood. For example, particle load may be expressed as the number of virus particles per milliliter of, e.g., blood. Particle load testing may be performed using nucleic acid amplification based tests, as well as non-nucleic acid-based tests (see, e.g., Puren et al., The Journal of Infectious Diseases, 201:S27-36 (2010)).

The term "mammal" refers to any mammalian species such as a human, mouse, rat, dog, cat, hamster, guinea pig, rabbit, livestock, and the like.

DESCRIPTION OF CERTAIN EMBODIMENTS

The present invention provides gRNA molecules that target the expression of one or more target genes, nucleic acid-lipid particles comprising one or more (e.g., a cocktail) of the gRNAs, and methods of delivering and/or administering the nucleic acid-lipid particles. The gRNA molecules may be delivered concurrently with or sequentially with a mRNA molecule that encodes Cas9, thereby delivering components to utilize the CRISPR/Cas9 system to treat disease in a human in need of such treatment. The Cas9 mRNA and gRNA may be present in the same nucleic acid-lipid particle, or they may be present in different nucleic acid-lipid particles.

In one aspect, the present invention provides gRNA molecules that target expression of one or more genes. In certain instances, the present invention provides compositions comprising a combination (e.g., a cocktail, pool, or mixture) of gRNAs that target different regions of an identified gene or genome.

The present invention also provides a pharmaceutical composition comprising one or more (e.g., a cocktail) of the gRNAs described herein and a pharmaceutically acceptable carrier.

In certain embodiments, a composition described herein comprises one or more gRNA molecules, which silences expression of a target gene.

In another aspect, the present invention provides a nucleic acid-lipid particle that targets gene expression of a specifically identified gene that causes a disease or disorder. The nucleic acid-lipid particles typically comprise one or more (e.g., a cocktail) of the molecules described herein, a cationic lipid, and a non-cationic lipid. In certain instances, the nucleic acid-lipid particles further comprise a conjugated lipid that inhibits aggregation of particles. The nucleic acid-lipid particles may comprise one or more (e.g., a cocktail) of the molecules described herein, a cationic lipid, a non-cationic lipid, and a conjugated lipid that inhibits aggregation of particles.

In some embodiments, the gRNAs of the present invention are fully encapsulated in the nucleic acid-lipid particle. With respect to formulations comprising an gRNA cocktail, the different types of gRNA species present in the cocktail (e.g., gRNA compounds with different sequences) may be co-encapsulated in the same particle, or each type of gRNA species present in the cocktail may be encapsulated in a separate particle. The gRNA cocktail may be formulated in the particles described herein using a mixture of two, three or more individual gRNAs (each having a unique sequence) at identical, similar, or different concentrations or molar ratios. In one embodiment, a cocktail of gRNAs (corresponding to a plurality of gRNAs with different sequences) is formulated using identical, similar, or different concentrations or molar ratios of each gRNA species, and the different types of gRNAs are co-encapsulated in the same particle. In another embodiment, each type of gRNA species present in the cocktail is encapsulated in different particles at identical, similar, or different gRNA concentrations or molar ratios, and the particles thus formed (each containing a different gRNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the nucleic acid-lipid particles of the invention may comprise, e.g., one or more cationic lipids of Formula I-III described herein or any other cationic lipid species. In one embodiment, cationic lipid is a dialkyl lipid. In another embodiment, the cationic lipid is a trialkyl lipid. In one particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA; Compound (15)), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), dilinoleylmethyl-3-dimethylaminopropionate (DLin-M-C2-DMA), (6Z,9Z,28Z,31Z)-heptatriaconta-6,9,28,31-tetraen-19-yl 4-(dimethylamino)butanoate (DLin-M-C3-DMA; Compound (7)), salts thereof, and mixtures thereof.

In another particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA; Compound (15)), 3-((6Z,9Z,28Z,31Z)-heptatriaconta-6,9,28,31-tetraen-19-yloxy)-N,N-dimethylpropan-1-amine (DLin-MP-DMA; Compound (8)), (6Z,9Z,28Z,31Z)-heptatriaconta-6,9,28,31-tetraen-19-yl 4-(dimethylamino)butanoate) (Compound (7)), (6Z,6Z)-12-((Z)-dec-4-enyl)docosa-6,16-dien-11-yl 5-(dimethylamino)pentanoate (Compound (13)), a salt thereof, or a mixture thereof.

In certain embodiments, the cationic lipid comprises from about 48 mol % to about 62 mol % of the total lipid present in the particle.

The non-cationic lipid in the nucleic acid-lipid particles of the present invention may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a preferred embodiment, the non-cationic lipid is a mixture of DPPC and cholesterol. In a preferred embodiment, the non-cationic lipid is a mixture of DSPC and cholesterol.

In certain embodiments, the non-cationic lipid comprises a mixture of a phospholipid and cholesterol or a derivative thereof, wherein the phospholipid comprises from about 7 mol % to about 17 mol % of the total lipid present in the particle and the cholesterol or derivative thereof comprises from about 25 mol % to about 40 mol % of the total lipid present in the particle.

The lipid conjugate in the nucleic acid-lipid particles of the invention inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof. In certain embodiments, the PEG-lipid conjugate is a PEG-DAA conjugate. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In certain embodiments, wherein the PEG-DAA conjugate is a PEG-dimyristyloxypropyl ($C_{14}$) conjugate. In another embodiment, the PEG-DAA conjugate is a compound (66) (PEG-C-DMA) conjugate. In another embodiment, the lipid conjugate comprises a POZ-lipid conjugate such as a POZ-DAA conjugate.

In certain embodiments, the conjugated lipid that inhibits aggregation of particles comprises from about 0.5 mol % to about 3 mol % of the total lipid present in the particle.

In certain embodiments, the nucleic acid-lipid particle has a total lipid:gRNA mass ratio of from about 5:1 to about 15:1.

In certain embodiments, the nucleic acid-lipid particle has a median diameter of from about 30 nm to about 150 nm.

In certain embodiments, the nucleic acid-lipid particle has an electron dense core.

In some embodiments, the present invention provides nucleic acid-lipid particles comprising: (a) one or more (e.g., a cocktail) gRNA molecules described herein; (b) one or more cationic lipids or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more (e.g., a cocktail) gRNA molecules described herein; (b) a cationic lipid or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. In one particular embodiment, the formulation is a four-component system comprising about 1.4 mol % PEG-lipid conjugate (e.g., PEG2000-C-DMA), about 57.1 mol % cationic lipid (e.g., DLin-K-C2-DMA) or a salt thereof, about 7.1 mol % DPPC (or DSPC), and about 34.3 mol % cholesterol (or derivative thereof).

In another aspect of this embodiment, the nucleic acid-lipid particle comprises: (a) one or more (e.g., a cocktail) gRNA molecules described herein; (b) a cationic lipid or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. In one particular embodiment, the formulation is a three-component system which is phospholipid-free and comprises about 1.5 mol % PEG-lipid conjugate (e.g., PEG2000-C-DMA), about 61.5 mol % cationic lipid (e.g., DLin-K-C2-DMA) or a salt thereof, and about 36.9 mol % cholesterol (or derivative thereof).

Additional formulations are described in PCT Publication No. WO 09/127060 and published US patent application publication number US 2011/0071208 A1, the disclosures of which are herein incorporated by reference in their entirety for all purposes.

In other embodiments, the present invention provides nucleic acid-lipid particles comprising: (a) one or more (e.g., a cocktail) gRNA molecules described herein; (b) one or more cationic lipids or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) gRNA molecules described herein; (b) a cationic lipid or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. In one particular embodiment, the formulation is a four-component system which comprises about 2 mol % PEG-lipid conjugate (e.g., PEG2000-C-DMA), about 40 mol % cationic lipid (e.g., DLin-K-C2-DMA) or a salt thereof, about 10 mol % DPPC (or DSPC), and about 48 mol % cholesterol (or derivative thereof).

In further embodiments, the present invention provides nucleic acid-lipid particles comprising: (a) one or more (e.g., a cocktail) gRNA molecules described herein; (b) one or more cationic lipids or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more (e.g., a cocktail) gRNA molecules described herein; (b) a cationic lipid or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. In certain instances, the non-cationic lipid mixture in the formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the formulation is a four-component system which comprises about 7 mol % PEG-lipid conjugate (e.g., PEG750-C-DMA), about 54 mol % cationic lipid (e.g., DLin-K-C2-DMA) or a salt thereof, about 7 mol % DPPC (or DSPC), and about 32 mol % cholesterol (or derivative thereof).

In another aspect of this embodiment, the nucleic acid-lipid particle comprises: (a) one or more (e.g., a cocktail)

gRNA molecules described herein; (b) a cationic lipid or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. In one particular embodiment, the formulation is a three-component system which is phospholipid-free and comprises about 7 mol % PEG-lipid conjugate (e.g., PEG750-C-DMA), about 58 mol % cationic lipid (e.g., DLin-K-C2-DMA) or a salt thereof, and about 35 mol % cholesterol (or derivative thereof).

Additional embodiments of useful formulations are described in published US patent application publication number US 2011/0076335 A1, the disclosure of which is herein incorporated by reference in its entirety for all purposes.

In certain embodiments of the invention, the nucleic acid-lipid particle comprises: (a) one or more (e.g., a cocktail) gRNA molecules described herein; (b) a cationic lipid or a salt thereof comprising from about 48 mol % to about 62 mol % of the total lipid present in the particle; (c) a mixture of a phospholipid and cholesterol or a derivative thereof, wherein the phospholipid comprises about 7 mol % to about 17 mol % of the total lipid present in the particle, and wherein the cholesterol or derivative thereof comprises about 25 mol % to about 40 mol % of the total lipid present in the particle; and (d) a PEG-lipid conjugate comprising from about 0.5 mol % to about 3.0 mol % of the total lipid present in the particle. Exemplary lipid formulations A-Z of this aspect of the invention are included below.

Exemplary lipid formulation A includes the following components (wherein the percentage values of the components are mole percent): PEG-lipid (1.2%), cationic lipid (53.2%), phospholipid (9.3%), cholesterol (36.4%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.2%), the cationic lipid is 1,2-dilinoleyloxy-N,N-dimethylaminopropane (DLinDMA) (53.2%), the phospholipid is DPPC (9.3%), and cholesterol is present at 36.4%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation A, which comprises one or more gRNA molecules described herein. For example, in certain embodiments, the nucleic acid lipid particle based on formulation A may comprise two different gRNA molecules, wherein a combination of the two different gRNA molecules is selected from any one of the combinations described herein. In certain other embodiments, the nucleic acid lipid particle based on formulation A may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation B which includes the following components (wherein the percentage values of the components are mole percent): PEG-lipid (0.8%), cationic lipid (59.7%), phospholipid (14.2%), cholesterol (25.3%), wherein the actual amounts of the lipids present may vary by, e.g., ±5% (or e.g., ±4 mol %, ±3 mol %, ±2 mol %, 11 mol %, ±0.75 mol %, ±0.5 mol %, ±0.25 mol %, or ±0.1 mol %). For example, in one representative embodiment, the PEG-lipid is PEG-C-DOMG (compound (67)) (0.8%), the cationic lipid is 1,2-dilinoleyloxy-N,N-dimethylaminopropane (DLinDMA) (59.7%), the phospholipid is DSPC (14.2%), and cholesterol is present at 25.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation B, which comprises one or more gRNA molecules described herein. For example, in certain embodiments, the nucleic acid lipid particle based on formulation B may comprise two different gRNA molecules, wherein a combination of the two different gRNA molecules is selected from any one of the combinations described herein. In certain other embodiments, the nucleic acid lipid particle based on formulation B may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation C includes the following components (wherein the percentage values of the components are mole percent): PEG-lipid (1.9%), cationic lipid (52.5%), phospholipid (14.8%), cholesterol (30.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.9%), the cationic lipid is 1,2-di-γ-linolenyloxy-N,N-dimethylaminopropane (γ-DLenDMA; Compound (15)) (52.5%), the phospholipid is DSPC (14.8%), and cholesterol is present at 30.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation C, which comprises one or more gRNA molecules described herein. For example, in certain embodiments, the nucleic acid lipid particle based on formulation C may comprise two different gRNA molecules, wherein a combination of the two different gRNA molecules is selected from any one of the combinations described herein. In certain other embodiments, the nucleic acid lipid particle based on formulation C may comprise three different gRNA molecules, wherein a combination of the three different gRNA molecules is selected from any one of the combinations described herein. In certain embodiments, the nucleic acid lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation D includes the following components (wherein the percentage values of the components are mole percent): PEG-lipid (0.7%), cationic lipid (60.3%), phospholipid (8.4%), cholesterol (30.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (0.7%), the cationic lipid is 3-((6Z,9Z,28Z,31Z)-heptatriaconta-6,9,28,31-tetraen-19-yloxy)-N,N-dimethylpropan-1-amine (DLin-MP-DMA; Compound (8) (60.3%), the phospholipid is DSPC (8.4%), and cholesterol is present at 30.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation D, which comprises one or more gRNA molecules described herein. For example, in certain embodiments, the nucleic acid lipid particle based on formulation D may comprise two different gRNA molecules, wherein a combination of the two different gRNA molecules is selected from any one of the combinations described herein. In certain other embodiments, the nucleic acid lipid particle based on formulation D may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation E includes the following components (wherein the percentage values of the components are mole percent): PEG-lipid (1.8%), cationic lipid (52.1%), phospholipid (7.5%), cholesterol (38.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.8%), the cationic lipid is (6Z,9Z,28Z,31Z)-heptatriaconta-6,9,28,31-tetraen-19-yl 4-(dimethylamino)butanoate) (Compound (7)) (52.1%), the phospholipid is DPPC (7.5%), and cholesterol is present at 38.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation E, which comprises one or more gRNA molecules described herein. For example, in certain embodiments, the nucleic acid lipid particle based on formulation E may comprise two different gRNA molecules, wherein a combination of the two different gRNA molecules is selected from any one of the combinations described herein. In certain other embodiments, the nucleic acid lipid particle based on formulation E may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary formulation F includes the following components (wherein the percentage values of the components are mole percent): PEG-lipid (0.9%), cationic lipid (57.1%), phospholipid (8.1%), cholesterol (33.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.9%), the cationic lipid is 1,2-dilinolenyloxy-N,N-dimethylaminopropane (DLenDMA), 1,2-di-γ-linolenyloxy-N,N-dimethylaminopropane (γ-DLenDMA; Compound (15)) (57.1%), the phospholipid is DSPC (8.1%), and cholesterol is present at 33.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation F, which comprises one or more gRNA molecules described herein. For example, in certain embodiments, the nucleic acid lipid particle based on formulation F may comprise two different gRNA molecules, wherein a combination of the two different gRNA molecules is selected from any one of the combinations described herein. In certain other embodiments, the nucleic acid lipid particle based on formulation F may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation G includes the following components (wherein the percentage values of the components are mole percent): PEG-lipid (1.7%), cationic lipid (61.6%), phospholipid (11.2%), cholesterol (25.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.7%), the cationic lipid is 1,2-dilinolenyloxy-N,N-dimethylaminopropane (DLenDMA), 1,2-di-γ-linolenyloxy-N,N-dimethylaminopropane (γ-DLenDMA; Compound (15)) (61.6%), the phospholipid is DPPC (11.2%), and cholesterol is present at 25.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation G, which comprises one or more gRNA molecules described herein. For example, in certain embodiments, the nucleic acid lipid particle based on formulation G may comprise two different gRNA molecules, wherein a combination of the two different gRNA molecules is selected from any one of the combinations described herein. In certain other embodiments, the nucleic acid lipid particle based on formulation G may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation H includes the following components (wherein the percentage values of the components are mole percent): PEG-lipid (1.1%), cationic lipid (55.0%), phospholipid (11.0%), cholesterol (33.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.1%), the cationic lipid is (6Z,16Z)-12-((Z)-dec-4-enyl)docosa-6,16-dien-11-yl 5-(dimethylamino)pentanoate (Compound (13)) (55.0%), the phospholipid is DSPC (11.0%), and cholesterol is present at 33.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation H, which comprises one or more gRNA molecules described herein. For example, in certain embodiments, the nucleic acid lipid particle based on formulation H may comprise two different gRNA molecules wherein a combination of the two different gRNA molecules is selected from any one of the combinations described herein. In certain other embodiments, the nucleic acid lipid particle based on formulation H may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation I includes the following components (wherein the percentage values of the components are mole percent): PEG-lipid (2.6%), cationic lipid (53.1%), phospholipid (9.4%), cholesterol (35.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.6%), the cationic lipid is (6Z,16Z)-12-((Z)-dec-4-enyl)docosa-6,16-dien-11-yl 5-(dimethylamino)pentanoate (Compound (13)) (53.1%), the phospholipid is DSPC (9.4%), and cholesterol is present at 35.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation I, which comprises one or more gRNA molecules described herein. For example, in certain embodiments, the nucleic acid lipid particle based on formulation I may comprise two different gRNA molecules, wherein a combination of the two different gRNA molecules is selected from any one of the combinations described herein. In certain other embodiments, the nucleic acid lipid particle based on formulation I may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation J includes the following components (wherein the percentage values of the components are mole percent): PEG-lipid (0.6%), cationic lipid (59.4%), phospholipid (10.2%), cholesterol (29.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (0.6%), the cationic lipid is 1,2-dilinoleyloxy-N,N-dimethylaminopropane (DLinDMA) (59.4%), the phospholipid is DPPC (10.2%), and cholesterol is present at 29.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation J, which comprises one or more gRNA molecules described herein. For example, in certain embodiments, the nucleic acid lipid particle based on formulation J may comprise two different gRNA molecules, wherein a combination of the two different gRNA molecules is selected from any one of the combinations described herein. In certain other embodiments, the nucleic acid lipid particle based on formulation J may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation K includes the following components (wherein the percentage values of the components are mole percent): PEG-lipid (0.5%), cationic lipid (56.7%), phospholipid (13.1%), cholesterol (29.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.5%), the cationic lipid is (6Z,9Z,28Z,31Z)-heptatriaconta-6,9,28,31-tetraen-19-yl 4-(dimethylamino)butanoate) (Compound (7)) (56.7%), the phospholipid is DSPC (13.1%), and cholesterol is present at 29.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation K, which comprises one or more gRNA molecules described herein. For example, in certain embodiments, the nucleic acid lipid particle based on formulation K may comprise two different gRNA molecules, wherein a combination of the two different gRNA molecules is selected from any one of the combinations described herein. In certain other embodiments, the nucleic acid lipid particle based on formulation K may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation L includes the following components (wherein the percentage values of the components are mole percent): PEG-lipid (2.2%), cationic lipid (52.0%), phospholipid (9.7%), cholesterol (36.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.2%), the cationic lipid is 1,2-di-γ-linolenyloxy-N,N-dimethylaminopropane (γ-DLenDMA; Compound (15)) (52.0%), the phospholipid is DSPC (9.7%), and cholesterol is present at 36.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation L, which comprises one or more gRNA molecules described herein. For example, in certain embodiments, the nucleic acid lipid particle based on formulation L may comprise two different gRNA molecules, wherein a combination of the two different gRNA molecules is selected from any one of the combinations described herein. In certain other embodiments, the nucleic acid lipid particle based on formulation L may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation M includes the following components (wherein the percentage values of the components are mole percent): PEG-lipid (2.7%), cationic lipid (58.4%), phospholipid (13.1%), cholesterol (25.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.7%), the cationic lipid is 1,2-dilinoleyloxy-N,N-dimethylaminopropane (DLinDMA) (58.4%), the phospholipid is DPPC (13.1%), and cholesterol is present at 25.7%, wherein the actual amounts of the lipids present may vary by, e.g., ±5% (or e.g., 4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation M, which comprises one or more gRNA molecules described herein. For example, in certain embodiments, the nucleic acid lipid particle based on formulation M may comprise two different gRNA molecules, wherein a combination of the two different gRNA molecules is selected from any one of the combinations described herein. In certain other embodiments, the nucleic acid lipid particle based on formulation M may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation N includes the following components (wherein the percentage values of the components are mole percent): PEG-lipid (3.0%), cationic lipid (53.3%), phospholipid (12.1%), cholesterol (31.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (3.0%), the cationic lipid is 1,2-dilinoleyloxy-N,N-dimethylaminopropane (DLinDMA) (53.3%), the phospholipid is DPPC (12.1%), and cholesterol is present at 31.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation N, which comprises one or more gRNA molecules described herein. For example, in certain embodiments, the nucleic acid lipid particle based on formulation N may comprise two different gRNA molecules, wherein a combination of the two different gRNA molecules is selected from any one of the combinations described herein. In certain other embodiments, the nucleic acid lipid particle based on formulation N may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation O includes the following components (wherein the percentage values of the components are mole percent): PEG-lipid (1.5%), cationic lipid (56.2%), phospholipid (7.8%), cholesterol (34.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.5%), the cationic lipid is 1,2-dilinoleyloxy-N,N-dimethylaminopropane (DLinDMA) (56.2%), the phospholipid is DPPC (7.8%), and cholesterol is present at 34.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation O, which comprises one or more gRNA molecules described herein. For example, in certain embodiments, the nucleic acid lipid particle based on formulation O may comprise two different gRNA molecules, wherein a combination of the two different gRNA molecules is selected from any one of the combinations described herein. In certain other embodiments, the nucleic acid lipid particle based on formulation O may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation P includes the following components (wherein the percentage values of the components are mole percent): PEG-lipid (2.1%), cationic lipid (48.6%), phospholipid (15.5%), cholesterol (33.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.1%), the cationic lipid is 3-((6Z,9Z,28Z,31Z)-heptatriaconta-6,9,28,31-tetraen-19-yloxy)-N,N-dimethylpropan-1-amine (DLin-MP-DMA; Compound (8)) (48.6%), the phospholipid is DSPC (15.5%), and cholesterol is present at 33.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation P, which comprises one or more gRNA molecules described herein. For example, in certain embodiments, the nucleic acid lipid particle based on formulation P may comprise two different gRNA molecules, wherein a combination of the two different gRNA molecules is selected from any one of the combinations described herein. In certain other embodiments, the nucleic acid lipid particle based on formulation P may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation Q includes the following components (wherein the percentage values of the components are mole percent): PEG-lipid (2.5%), cationic lipid (57.9%), phospholipid (9.2%), cholesterol (30.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.5%), the cationic lipid is (6Z,6Z)-12-((Z)-dec-4-enyl)docosa-6,16-dien-11-yl 5-(dimethylamino)pentanoate (Compound (13)) (57.9%), the phospholipid is DSPC (9.2%), and cholesterol is present at 30.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation Q, which comprises one or more gRNA molecules described herein. For example, in certain embodiments, the nucleic acid lipid particle based on formulation Q may comprise two different gRNA molecules, wherein a combination of the two different gRNA molecules is selected from any one of the combinations described herein. In certain other embodiments, the nucleic acid lipid particle based on formulation Q may comprise three different gRNA molecules, wherein a combination of the two different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation R includes the following components (wherein the percentage values of the components are mole percent): PEG-lipid (1.6%), cationic lipid (54.6%), phospholipid (10.9%), cholesterol (32.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.6%), the cationic lipid is 3-((6Z,9Z,28Z,31Z)-heptatriaconta-6,9,28,31-tetraen-19-yloxy)-N,N-dimethylpropan-1-amine (Compound (8)) (54.6%), the phospholipid is DSPC (10.9%), and cholesterol is present at 32.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation R, which comprises one or more gRNA molecules described herein. For example, in certain embodiments, the nucleic acid lipid particle based on formulation R may comprise two different gRNA molecules, wherein a combination of the two different gRNA molecules is selected from any one of the combinations described herein.

In certain other embodiments, the nucleic acid lipid particle based on formulation R may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation S includes the following components (wherein the percentage values of the components are mole percent): PEG-lipid (2.9%), cationic lipid (49.6%), phospholipid (16.3%), cholesterol (31.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.9%), the cationic lipid is (6Z,16Z)-12-((Z)-dec-4-enyl)docosa-6,16-dien-11-yl 5-(dimethylamino)pentanoate (Compound (13)) (49.6%), the phospholipid is DPPC (16.3%), and cholesterol is present at 31.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation S, which comprises one or more gRNA molecules described herein. For example, in certain embodiments, the nucleic acid lipid particle based on formulation S may comprise two different gRNA molecules, wherein a combination of the two different gRNA molecules is selected from any one of the combinations described herein. In certain other embodiments, the nucleic acid lipid particle based on formulation S may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation T includes the following components (wherein the percentage values of the components are mole percent): PEG-lipid (0.7%), cationic lipid (50.5%), phospholipid (8.9%), cholesterol (40.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.7%), the cationic lipid is 1,2-dilinoleyloxy-N,N-dimethylaminopropane (DLinDMA) (50.5%), the phospholipid is DPPC (8.9%), and cholesterol is present at 40.0%, wherein the actual amounts of the lipids present may vary by, e.g., 5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation T, which comprises one or more gRNA molecules described herein. For example, in certain embodiments, the nucleic acid lipid particle based on formulation T may comprise two different gRNA molecules, wherein a combination of the two different gRNA molecules is selected from any one of the combinations described herein. In certain other embodiments, the nucleic acid lipid particle based on formulation T may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation U includes the following components (wherein the percentage values of the components are mole percent): PEG-lipid (1.0%), cationic lipid (51.4%), phospholipid (15.0%), cholesterol (32.6%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.0%), the cationic lipid is 1,2-dilinoleyloxy-N,N-dimethylaminopropane (DLinDMA) (51.4%), the phospholipid is DSPC (15.0%), and cholesterol is present at 32.6%, wherein the actual amounts of the lipids present may vary by, e.g., ±5% (or e.g., 4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation U, which comprises one or more gRNA molecules described herein. For example, in certain embodiments, the nucleic acid lipid particle based on formulation U may comprise two different gRNA molecules, wherein a combination of the two different gRNA molecules is selected from any one of the combinations described herein. In certain other embodiments, the nucleic acid lipid particle based on formulation U may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation V includes the following components (wherein the percentage values of the components are mole percent): PEG-lipid (1.3%), cationic lipid (60.0%), phospholipid (7.2%), cholesterol (31.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.3%), the cationic lipid is 1,2-dilinolenyloxy-N,N-dimethylaminopropane (DLenDMA) (60.0%), the phospholipid is DSPC (7.2%), and cholesterol is present at 31.5%, wherein the actual amounts of the lipids present may vary by, e.g., ±5% (or e.g., 4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation V, which comprises one or more gRNA molecules described herein. For example, in certain embodiments, the nucleic acid lipid particle based on formulation V may comprise two different gRNA molecules, wherein a combination of the two different gRNA molecules is selected from any one of the combinations described herein. In certain other embodiments, the nucleic acid lipid particle based on formulation V may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation W includes the following components (wherein the percentage values of the components are mole percent): PEG-lipid (1.8%), cationic lipid (51.6%), phospholipid (8.4%), cholesterol (38.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.8%), the cationic lipid is 1,2-dilinoleyloxy-N,N-dimethylaminopropane (DLinDMA) (51.6%), the phospholipid is DSPC (8.4%), and cholesterol is present at 38.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation W, which comprises one or more gRNA molecules described herein. For example, in certain embodiments, the nucleic acid lipid particle based on formulation W may comprise two different gRNA molecules, wherein a combination of the two different gRNA molecules is selected from any one of the combinations described herein. In certain other embodiments, the nucleic acid lipid particle based on formulation W may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation X includes the following components (wherein the percentage values of the components are mole percent): PEG-lipid (2.4%), cationic lipid (48.5%), phospholipid (10.0%), cholesterol (39.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.4%), the cationic lipid is 1,2-di-γ-linolenyloxy-N,N-dimethylaminopropane (γ-DLenDMA; Compound (15)) (48.5%), the phospholipid is DPPC (10.0%), and cholesterol is present at 39.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation X, which comprises one or more gRNA molecules described herein. For example, in certain embodiments, the nucleic acid lipid particle based on formulation X may comprise two different gRNA molecules, wherein a combination of the two different gRNA molecules is selected from any one of the combinations described herein. In certain other embodiments, the nucleic acid lipid particle based on formulation X may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation Y includes the following components (wherein the percentage values of the components are mole percent): PEG-lipid (2.6%), cationic lipid (61.2%), phospholipid (7.1%), cholesterol (29.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.6%), the cationic lipid is (6Z,16Z)-12-((Z)-dec-4-enyl)docosa-6,16-dien-11-yl 5-(dimethylamino)pentanoate (Compound (13)) (61.2%), the phospholipid is DSPC (7.1%), and cholesterol is present at 29.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation Y, which comprises one or more gRNA molecules described herein. For example, in certain embodiments, the nucleic acid lipid particle based on formulation Y may comprise two different gRNA molecules, wherein a combination of the two different gRNA molecules is selected from any one of the combinations described herein. In certain other embodiments, the nucleic acid lipid particle based on formulation Y may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation Z includes the following components (wherein the percentage values of the components are mole percent): PEG-lipid (2.2%), cationic lipid (49.7%), phospholipid (12.1%), cholesterol (36.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.2%), the cationic lipid is (6Z,9Z,28Z,31Z)-heptatriaconta-6,9,28,31-tetraen-19-yl 4-(dimethylamino)butanoate) (Compound (7)) (49.7%), the phospholipid is DPPC (12.1%), and cholesterol is present at 36.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation Z, which comprises one or more gRNA molecules described herein. For example, in certain embodiments, the nucleic acid lipid particle based on formulation Z may comprise two different gRNA molecules, wherein a combination of the two different gRNA molecules is selected from any one of the combinations described herein. In certain other embodiments, the nucleic acid lipid particle based on formulation Z may comprise three different gRNA molecules, wherein a combination of the three different gRNA molecules is selected from any one of the combinations described herein. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Accordingly, certain embodiments of the invention provide a nucleic acid-lipid particle described herein, wherein the lipids are formulated as described in any one of formulations A, B, C, D, E, F, G, H, I, J, K, L, M, N, O, P, Q, R, S, T, U, V, W, X, Y or Z.

The present invention also provides pharmaceutical compositions comprising a nucleic acid-lipid particle and a pharmaceutically acceptable carrier.

The nucleic acid-lipid particles of the present invention are useful, for example, for the therapeutic delivery of gRNAs that silence the expression of one or more target genes. In some embodiments, a cocktail of gRNAs that target different regions (e.g., overlapping and/or non-overlapping sequences) of a target gene or transcript is formulated into the same or different nucleic acid-lipid particles, and the particles are administered to a mammal (e.g., a human) requiring such treatment. In certain instances, a therapeutically effective amount of the nucleic acid-lipid particles can be administered to the mammal.

In certain embodiments, the present invention provides a method for introducing one or more gRNA molecules described herein into a cell by contacting the cell with a nucleic acid-lipid particle described herein.

In certain embodiments, the present invention provides a method for introducing one or more gRNA molecules that silence expression of a target gene into a cell by contacting the cell with a nucleic acid-lipid particle described herein under conditions whereby the gRNA enters the cell and silences the expression of the target gene within the cell. In certain embodiments, the cell is in a mammal, such as a human. In certain embodiments, the human has been diagnosed with a specific disease or disorder.

In certain embodiments, the present invention provides a method for silencing expression of a target gene in a cell, the method comprising the step of contacting a cell comprising an expressed target gene with a nucleic acid-lipid particle or a composition (e.g., a pharmaceutical composition) described herein under conditions whereby the gRNA enters the cell and silences the expression of the target gene within the cell. In certain embodiments, the cell is in a mammal, such as a human.

In some embodiments, the nucleic acid-lipid particles or compositions (e.g., a pharmaceutical composition) described herein are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In certain aspects, the present invention provides methods for silencing target gene expression in a mammal (e.g., human) in need thereof, the method comprising administering to the mammal a therapeutically effective amount of a nucleic acid-lipid particle comprising one or more gRNAs described herein. In some embodiments, administration of nucleic acid-lipid particles comprising one or more gRNAs described herein reduces target RNA levels by at least about 5%, 100%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to RNA levels detected in the absence of the gRNA (e.g., buffer control or irrelevant gRNA control). In other embodiments, administration of nucleic acid-lipid particles comprising one or more gRNAs reduces target RNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-targeting gRNA control.

In other aspects, the present invention provides methods for silencing target gene expression in a mammal (e.g., human) in need thereof, the method comprising administering to the mammal a therapeutically effective amount of a nucleic acid-lipid particle comprising one or more gRNAs described herein. In some embodiments, administration of nucleic acid-lipid particles comprising one or more gRNAs reduces target mRNA levels by at least about 5%, 100%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 1000% (or any range therein) relative to mRNA levels detected in the absence of the gRNA (e.g., buffer control or irrelevant non-targeting gRNA control). In other embodiments, administration of nucleic acid-lipid particles comprising one or more gRNAs reduces target mRNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-targeting gRNA control.

Certain embodiments of the invention provide a nucleic acid-lipid particle or a composition (e.g., a pharmaceutical composition) described herein for use in silencing expression of a target gene in a cell in a mammal (e.g., a human).

Certain embodiments of the invention provide the use of a nucleic acid-lipid particle or a composition (e.g., a pharmaceutical composition) described herein to prepare a medicament for silencing expression of a target gene in a cell in a mammal (e.g., a human).

In other aspects, the present invention provides methods for treating, preventing, reducing the risk or likelihood of developing (e.g., reducing the susceptibility to), delaying the onset of, and/or ameliorating one or more symptoms associated with a disease in a mammal (e.g., human) in need thereof, the method comprising administering to the mammal a therapeutically effective amount of a nucleic acid-lipid particle comprising one or more gRNA molecules described herein that target gene expression.

Certain embodiments of the invention provide a nucleic acid-lipid particle or a composition (e.g., a pharmaceutical composition) for use in treating a disease in a mammal (e.g., a human).

Certain embodiments of the invention provide the use of a nucleic acid-lipid particle or a composition (e.g., a pharmaceutical composition) to prepare a medicament for treating a disease in a mammal (e.g., a human).

Certain embodiments of the invention provide a method for ameliorating one or more symptoms associated with a disease in a mammal, the method comprising the step of administering to the mammal a therapeutically effective amount of a nucleic acid-lipid particle or composition (e.g., a pharmaceutical composition) described herein, comprising one or more gRNA molecules. In certain embodiments, the particle is administered via a systemic route.

Certain embodiments of the invention provide a nucleic acid-lipid particle or a composition (e.g., a pharmaceutical composition) as described herein for use in ameliorating one or more symptoms associated with a disease in a mammal (e.g., a human).

Certain embodiments of the invention provide the use of a nucleic acid-lipid particle or a composition (e.g., a pharmaceutical composition) as described herein to prepare a medicament for ameliorating one or more symptoms associated with a disease in a mammal (e.g., a human).

Certain embodiments of the invention provide a nucleic acid-lipid particle or a composition (e.g., a pharmaceutical composition) as described herein for use in medical therapy.

In some embodiments, administration of nucleic acid-lipid particles comprising one or more gRNAs lowers, reduces, or decreases target protein levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to the target protein levels detected in the absence of the gRNA.

By way of example, mRNA can be measured using a branched DNA assay (QuantiGene®; Affymetrix). The branched DNA assay is a sandwich nucleic acid hybridization method that uses bDNA molecules to amplify signal from captured target RNA.

In addition to its utility in silencing the expression of any of the target genes for therapeutic purposes, the lipid nanoparticles described herein are also useful in research and development applications as well as diagnostic, prophylactic, prognostic, clinical, and other healthcare applications. As a non-limiting example, the gRNA can be used in target validation studies directed at testing whether a specific member of a gene family has the potential to be a therapeutic target.

Generating gRNA Molecules

In some embodiments, gRNA may be produced enzymatically or by partial/total organic synthesis, and modified ribonucleotides can be introduced by in vitro enzymatic or organic synthesis. In certain instances, the gRNA is prepared chemically. Methods of synthesizing nucleic acid molecules are known in the art, e.g., the chemical synthesis methods as described in Verma and Eckstein (1998) or as described herein.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, gRNA are chemically synthesized. The oligonucleotides that comprise the gRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

Carrier Systems Containing Therapeutic Nucleic Acids
A. Lipid Particles

In certain aspects, the present invention provides lipid particles comprising one or more gRNA molecules and one or more of cationic (amino) lipids or salts thereof. In some embodiments, the lipid particles of the invention further comprise one or more non-cationic lipids. In other embodiments, the lipid particles further comprise one or more conjugated lipids capable of reducing or inhibiting particle aggregation.

The lipid particles of the invention may comprise one or more gRNA, a cationic lipid, a non-cationic lipid, and a conjugated lipid that inhibits aggregation of particles. In some embodiments, the gRNA molecule is fully encapsulated within the lipid portion of the lipid particle such that the gRNA molecule in the lipid particle is resistant in aqueous solution to nuclease degradation. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. In certain embodiments, the lipid particles of the invention have a median diameter of from about 30 nm to about 150 nm. The lipid particles of the invention also typically have a lipid:nucleic acid ratio (e.g., a lipid:gRNA ratio) (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1. In certain embodiments, the nucleic acid-lipid particle has a lipid:gRNA mass ratio of from about 5:1 to about 15:1.

In preferred embodiments, the lipid particles of the invention are serum-stable nucleic acid-lipid particles which comprise one or more gRNA molecules, a cationic lipid (e.g., one or more cationic lipids of Formula I-III or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The lipid particle may comprise at least 1, 2, 3, 4, 5, 6, 7, 8, 9, 10, or more gRNA molecules that target one or more of the genes described herein. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the one or more gRNA molecules may be fully encapsulated within the lipid portion of the particle, thereby protecting the gRNA from nuclease degradation. In certain instances, the gRNA in the nucleic acid-lipid particle is not substantially degraded after exposure of the particle to a nuclease at 37° C. for at least about 20, 30, 45, or 60 minutes. In certain other instances, the gRNA in the nucleic acid-lipid particle is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the gRNA is complexed with the lipid portion of the particle. One of the benefits of the formulations of the present invention is that the nucleic acid-lipid particle compositions are substantially non-toxic to mammals such as humans.

The term "fully encapsulated" indicates that the gRNA in the nucleic acid-lipid particle is not significantly degraded after exposure to serum or a nuclease assay that would significantly degrade free DNA or RNA. In a fully encapsulated system, preferably less than about 25% of the gRNA in the particle is degraded in a treatment that would normally degrade 100% of free gRNA, more preferably less than about 10%, and most preferably less than about 5% of the gRNA in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle composition comprising a plurality of nucleic acid-lipid particles.

In some instances, the nucleic acid-lipid particle composition comprises a gRNA molecule that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the gRNA encapsulated therein.

In other instances, the nucleic acid-lipid particle composition comprises gRNA that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input gRNA is encapsulated in the particles.

Depending on the intended use of the lipid particles of the invention, the proportions of the components can be varied and the delivery efficiency of a particular formulation can be measured using, e.g., an endosomal release parameter (ERP) assay.

1. Cationic Lipids

Any of a variety of cationic lipids or salts thereof may be used in the lipid particles of the present invention either alone or in combination with one or more other cationic lipid species or non-cationic lipid species. The cationic lipids include the (R) and/or (S) enantiomers thereof.

In one aspect of the invention, the cationic lipid is a dialkyl lipid. For example, dialkyl lipids may include lipids that comprise two saturated or unsaturated alkyl chains, wherein each of the alkyl chains may be substituted or unsubstituted. In certain embodiments, each of the two alkyl chains comprise at least, e.g., 8 carbon atoms, 10 carbon atoms, 12 carbon atoms, 14 carbon atoms, 16 carbon atoms, 18 carbon atoms, 20 carbon atoms, 22 carbon atoms or 24 carbon atoms.

In one aspect of the invention, the cationic lipid is a trialkyl lipid. For example, trialkyl lipids may include lipids that comprise three saturated or unsaturated alkyl chains, wherein each of the alkyl chains may be substituted or unsubstituted. In certain embodiments, each of the three alkyl chains comprise at least, e.g., 8 carbon atoms, 10 carbon atoms, 12 carbon atoms, 14 carbon atoms, 16 carbon atoms, 18 carbon atoms, 20 carbon atoms, 22 carbon atoms or 24 carbon atoms.

In one aspect, cationic lipids of Formula I having the following structure are useful in the present invention:

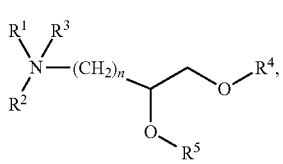

(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, wherein at least one of $R^4$ and $R^5$ comprises at least two sites of unsaturation.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, an arachidonyl moiety, and a docosahexaenoyl moiety, as well as acyl derivatives thereof (e.g., linoleoyl, linolenoyl, γ-linolenoyl, etc.). In some instances, one of $R^4$ and $R^5$ comprises a branched alkyl group (e.g., a phytanyl moiety) or an acyl derivative thereof (e.g., a phytanoyl moiety). In certain instances, the octadecadienyl moiety is a linoleyl moiety. In certain other instances, the octadecatrienyl moiety is a linolenyl moiety or a γ-linolenyl moiety. In certain embodiments, $R^4$ and $R^5$ are both linoleyl moieties, linolenyl moieties, or γ-linolenyl moieties. In particular embodiments, the cationic lipid of Formula I is 1,2-dilinoleyloxy-N,N-dimethylaminopropane (DLinDMA), 1,2-dilinolenyloxy-N,N-dimethylaminopropane (DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes. The synthesis of cationic lipids such as C2-DLinDMA and C2-DLinDAP, as well as additional cationic lipids, is described in international patent application number WO2011/000106 the disclosure of which is herein incorporated by reference in its entirety for all purposes.

In another aspect, cationic lipids of Formula II having the following structure (or salts thereof) are useful in the present invention:

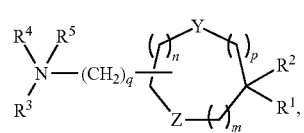

(II)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH. In a preferred embodiment, q is 2.

In some embodiments, the cationic lipid of Formula II is 2,2-dilinoleyl-4-(2-dimethylaminoethyl)-[1,3]-dioxolane (DLin-K-C2-DMA; "XTC2" or "C2K"), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis (dimethylaminomethyl)-[1,3]-dioxolane (DLin-K$^2$-DMA), 2,2-dilinoleyl-4-methylpiperzine-[1,3]-dioxolane (D-Lin-K-N-methylpiperzine), or mixtures thereof. In preferred embodiments, the cationic lipid of Formula II is DLin-K-C2-DMA.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLin-K-DMA, as well as additional cationic lipids, is described in PCT Publication No. WO 09/086558, the disclosure of which is herein incorporated by reference in its entirety for all purposes. The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K²-DMA, and D-Lin-K-N-methylpiperzine, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes.

In a further aspect, cationic lipids of Formula III having the following structure are useful in the present invention:

In an alternative embodiment, the cationic lipid of Formula III comprises ester linkages between the amino head group and one or both of the alkyl chains. In some embodiments, the cationic lipid of Formula III forms a salt (preferably a crystalline salt) with one or more anions. In one particular embodiment, the cationic lipid of Formula III is the oxalate (e.g., hemioxalate) salt thereof, which is preferably a crystalline salt.

Although each of the alkyl chains in Formula III contains cis double bonds at positions 6, 9, and 12 (i.e., cis,cis,cis-$\Delta^6,\Delta^9,\Delta^{12}$), in an alternative embodiment, one, two, or three of these double bonds in one or both alkyl chains may be in the trans configuration.

In a particularly preferred embodiment, the cationic lipid of Formula III has the structure:

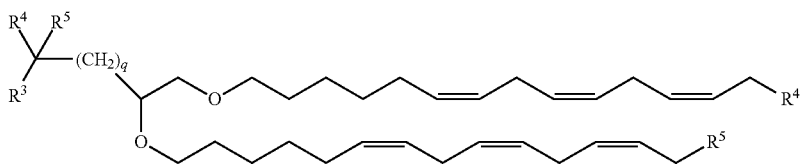

(III)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

The synthesis of cationic lipids such as γ-DLenDMA (15), as well as additional cationic lipids, is described in U.S.

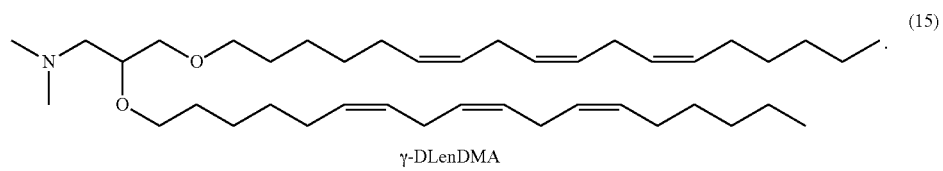 [SMILES: CCCCC/C=C\C/C=C\C/C=C\CCCCCOCC(CN(C)C)OCCCCC/C=C\C/C=C\C/C=C\CCCCC]

(15)

γ-DLenDMA

Provisional Application No. 61/222,462, entitled "Improved Cationic Lipids and Methods for the Delivery of Nucleic Acids," filed Jul. 1, 2009, the disclosure of which is herein incorporated by reference in its entirety for all purposes.

The synthesis of cationic lipids such as DLin-M-C3-DMA ("MC3"), as well as additional cationic lipids (e.g., certain analogs of MC3), is described in U.S. Provisional Application No. 61/185,800, entitled "Novel Lipids and Compositions for the Delivery of Therapeutics," filed Jun. 10, 2009, and U.S. Provisional Application No. 61/287,995, entitled "Methods and Compositions for Delivery of Nucleic Acids," filed Dec. 18, 2009, the disclosures of which are herein incorporated by reference in their entirety for all purposes.

Examples of other cationic lipids or salts thereof which may be included in the lipid particles of the present invention include, but are not limited to, cationic lipids such as those described in WO2011/000106, the disclosure of which is herein incorporated by reference in its entirety for all purposes, as well as cationic lipids such as N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), dilinoleylmethyl-3-dimethylaminopropionate (DLin-M-C2-DMA; also known as DLin-M-K-DMA or DLin-M-DMA), and mixtures thereof. Additional cationic lipids or salts thereof which may be included in the lipid particles of the present invention are described in U.S. Patent Publication No. 20090023673, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes. The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes. The synthesis of cationic lipids such as DO-C-DAP, DMDAP, DOTAP.Cl, DLin-M-C2-DMA, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes. The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from Invitrogen); LIPOFECTAMINE® (including DOSPA and DOPE, available from Invitrogen); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in one exemplary lipid particle formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle; however, one skilled in the art will understand that the total mol % may deviate slightly from 100% due to rounding, for example, 99.9 mol % or 100.1 mol %.).

Further examples of cationic lipids useful for inclusion in lipid particles used in the present invention are shown below:

(5)

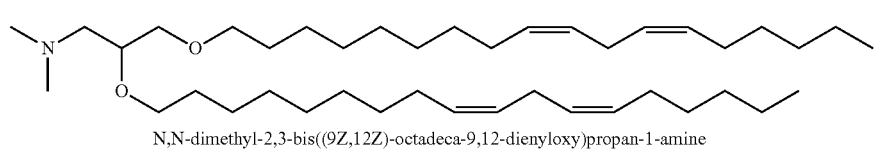

N,N-dimethyl-2,3-bis((9Z,12Z)-octadeca-9,12-dienyloxy)propan-1-amine

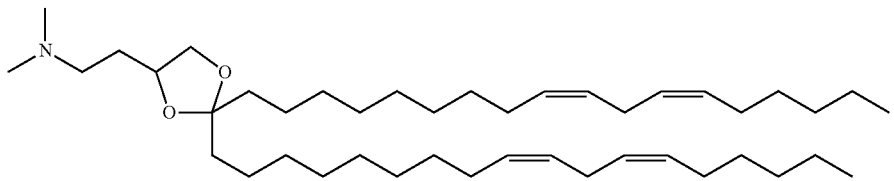

2-(2,2-di((9Z,12Z)-octadeca-9,12-dienyl)-1,3-dioxolan-4-yl)-N,N-dimethylethanamine  (6)

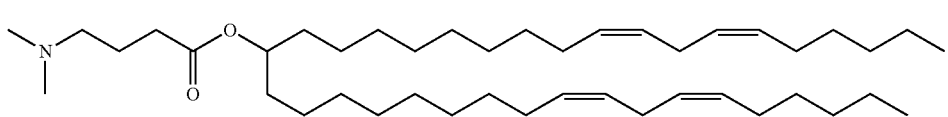

(6Z,9Z,28Z,31Z)-heptatriaconta-6,9,28,31-tetraen-19-yl 4-(dimethylamino)butanoate  (7)

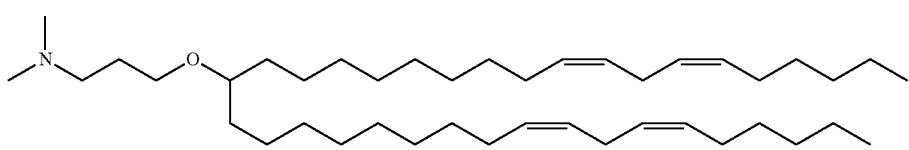

3-((6Z,9Z,28Z,31Z)-heptatriaconta-6,9,28,31-tetraen-19-yloxy)-N,N-dimethylpropan-1-amine  (8)

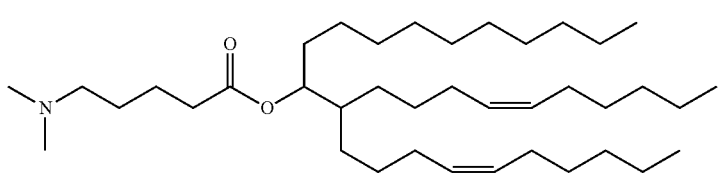

(Z)-12-((Z)-dec-4-enyl)docos-16-en-11-yl 5-(dimethylamino)pentanoate  (53)

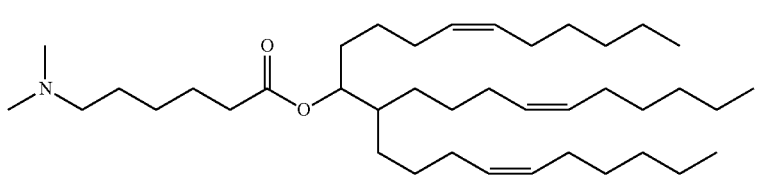

(6Z,16Z)-12-((Z)-dec-4-enyl)docosa-6,16-dien-11-yl 6-(dimethylamino)hexanoate  (11)

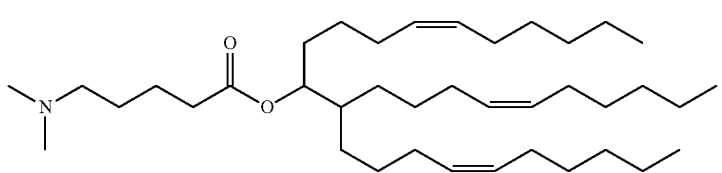

(6Z,16Z)-12-((Z)-dec-4-enyl)docosa-6,16-dien-11-yl 5-(dimethylamino)pentanoate  (13)

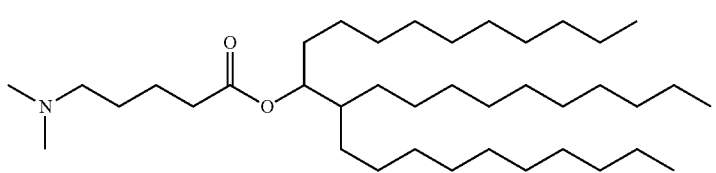

12-decyldocosan-11-yl 5-(dimethylamino)pentanoate  (14)

2. Non-Cationic Lipids

The non-cationic lipids used in the lipid particles of the invention can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyl-oxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 45 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In an certain embodiments, the phospholipid component in the mixture comprises from about 5 mol % to about 17 mol %, from about 7 mol % to about 17 mol %, from about 7 mol % to about 15 mol %, from about 8 mol % to about 15 mol %, or about 8 mol %, 9 mol %, 10 mol %, 11 mol %, 12 mol %, 13 mol %, 14 mol %, or 15 mol % (or any fraction thereof or range therein) of the total lipid present in the particle. As a non-limiting example, a lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

By way of further example, a lipid formulation useful in the practice of the invention has a lipid to drug (e.g., gRNA) ratio of about 10:1 (e.g., a lipid:drug ratio of from 9.5:1 to 11:1, or from 9.9:1 to 11:1, or from 10:1 to 10.9:1). In certain other embodiments, a lipid formulation useful in the practice of the invention has a lipid to drug (e.g., gRNA) ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a lipid particle formulation may comprise cholesterol at about 37 mol % (or any fraction thereof) of the total lipid present in the particle. As another non-limiting example, a lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %, ±4 mol %, ±3 mol %, ±2 mol %, ±1 mol %, ±0.75 mol %, ±0.5 mol %, ±0.25 mol %, or ±0.1 mol %.

3. Lipid Conjugates

In addition to cationic and non-cationic lipids, the lipid particles of the invention may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-di-oxaoctanyl]carbamoyl-ω-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxy-polyethylene glycol-amine (MePEG-$NH_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-$NH_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-$CH_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CC$H_2$C$H_2$C(O)—), succinamidyl (—NHC(O)C$H_2$C$H_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skill in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

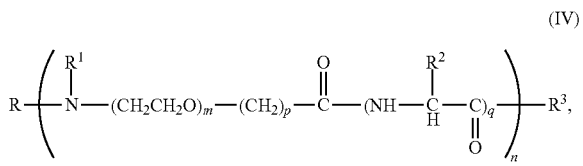

(IV)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

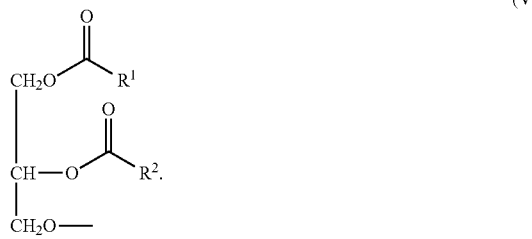

(V)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(VI)

In a preferred embodiment, the PEG-lipid is a PEG-DAA conjugate having the following formula:

(VII)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VII above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

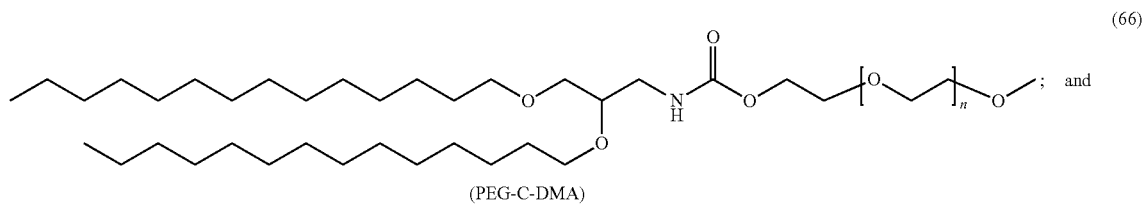

(PEG-C-DMA) (66)

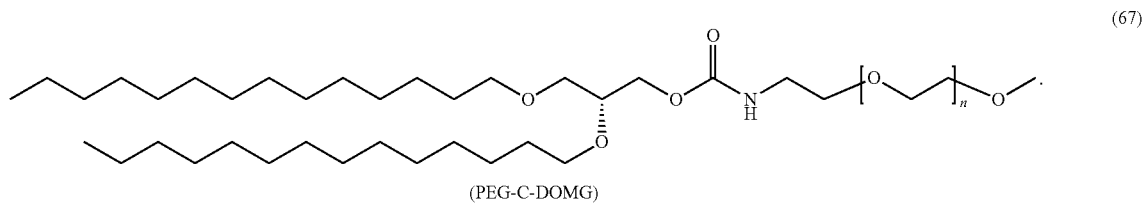

(PEG-C-DOMG) (67)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles of the present invention can further comprise cationic poly(ethylene glycol) (PEG) lipids or CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

Suitable CPLs include compounds of Formula VIII:

$$A\text{-}W\text{-}Y \quad \quad \quad (VIII),$$

wherein A, W, and Y are as described below.

With reference to Formula VIII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 3 mol %, from about 0.5 mol % to about 3 mol %, or about 0.6 mol %, 0.7 mol %, 0.8 mol %, 0.9 mol %, 1.0 mol %, 1.1 mol %, 1.2 mol %, 1.3 mol %, 1.4 mol %, 1.5 mol %, 1.6 mol %, 1.7 mol %, 1.8 mol %, 1.9 mol %, 2.0 mol %, 2.1 mol %, 2.2 mol %, 2.3 mol %, 2.4 mol %, 2.5 mol %, 2.6 mol %, 2.7 mol %, 2.8 mol %, 2.9 mol % or 3 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

It should be understood that the percentage of lipid conjugate present in the lipid particles of the invention is a target amount, and that the actual amount of lipid conjugate present in the formulation may vary, for example, by ±5 mol %, ±4 mol %, ±3 mol %, ±2 mol %, ±1 mol %, ±0.75 mol %, ±0.5 mol %, ±0.25 mol %, or ±0.1 mol %.

Additional percentages and ranges of lipid conjugates suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Preparation of Lipid Particles

The nucleic acid-lipid particles of the present invention, in which a nucleic acid (e.g., a gRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise lipids of Formula I-III or salts thereof, alone or in combination with other cationic lipids. In other embodiments, the non-cationic lipids are egg sphingomyelin (ESM), distearoylphosphatidylcholine (DSPC), dioleoyl-phosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (l-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles produced via a continuous mixing method, e.g., a process that includes providing an aqueous solution comprising a gRNA in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the gRNA within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 1800 flows; however, connectors providing shallower angles can be used, e.g., from about 27° to about 1800 (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles (e.g., the gRNA molecules) are precondensed as described in, e.g., U.S. patent application Ser. No. 09/744, 103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid (e.g., gRNA) to lipid ratios (mass/mass ratios) in a formed nucleic acid-lipid particle will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid (e.g., gRNA) ratios (mass/mass ratios) in a formed nucleic acid-lipid particle will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making lipid particle-CPLs (CPL-containing lipid particles) are discussed herein. Two general techniques include the "post-insertion" technique, that is, insertion of a CPL into, for example, a pre-formed lipid particle, and the "standard" technique, wherein the CPL is included in the lipid mixture during, for example, the lipid particle formation steps. The post-insertion technique results in lipid particles having CPLs mainly in the external face of the lipid particle bilayer membrane, whereas standard techniques provide lipid particles having CPLs on both internal and external faces. The method is especially useful for vesicles made from phospholipids (which can contain cholesterol) and also for vesicles containing PEG-lipids (such as PEG-DAAs and PEG-DAGs). Methods of making lipid particle-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

Kits

The present invention also provides lipid particles in kit form. In some embodiments, the kit comprises a container which is compartmentalized for holding the various elements of the lipid particles (e.g., the active agents, such as gRNA molecules and the individual lipid components of the particles). Preferably, the kit comprises a container (e.g., a vial or ampoule) which holds the lipid particles of the invention, wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

The formulations of the present invention can be tailored to preferentially target particular cells, tissues, or organs of interest. Preferential targeting of a nucleic acid-lipid particle may be carried out by controlling the composition of the lipid particle itself. In particular embodiments, the kits of the invention comprise these lipid particles, wherein the particles are present in a container as a suspension or in dehydrated form.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

Administration of Lipid Particles

Once formed, the lipid particles of the invention are particularly useful for the introduction of a gRNA molecule into cells. Accordingly, the present invention also provides methods for introducing a gRNA molecule into a cell in combination with an mRNA encoding a Cas9. In particular embodiments, the gRNA molecule and mRNA encoding a Cas9 are introduced into an infected cell. The methods may be carried out in vitro or in vivo by first forming the particles as described above and then contacting the particles with the cells for a period of time sufficient for delivery of gRNA to the cells to occur.

The lipid particles of the invention (e.g., a nucleic-acid lipid particle) can be adsorbed to almost any cell type with which they are mixed or contacted. Once adsorbed, the particles can either be endocytosed by a portion of the cells, exchange lipids with cell membranes, or fuse with the cells. Transfer or incorporation of the gRNA portion of the particle can take place via any one of these pathways. In particular, when fusion takes place, the particle membrane is integrated into the cell membrane and the contents of the particle combine with the intracellular fluid.

The lipid particles of the invention (e.g., nucleic acid-lipid particles) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention are particularly useful in methods for the therapeutic delivery of one or more gRNA molecules. In particular, it is an object of this invention to provide in vivo methods for treatment of disease in humans by downregulating or silencing the transcription and/or translation of one or more target genes.

A. In Vivo Administration

Systemic delivery for in vivo therapy, e.g., delivery of a gRNA molecule described herein, to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the gRNA from nuclease degradation in serum, are non-immunogenic, are small in size, and are suitable for repeat dosing. Additionally, the one or more gRNA molecules may be administered alone in the lipid particles of the invention, or in combination (e.g., co-administered) with lipid particles comprising peptides, polypeptides, or small molecules such as conventional drugs.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a gRNA molecule is detectable in cells at about 8, 12, 24, 36, 48, 60, 72 or 96 hours after administration. In other embodiments, downregulation of expression of a target sequence, such as a viral or host sequence, by a gRNA molecule is detectable at about 8, 12, 24, 36, 48, 60, 72 or 96 hours after administration. In yet other embodiments, downregulation of expression of a target sequence, such as a viral or host sequence, by a gRNA molecule occurs preferentially in infected cells and/or cells capable of being infected. In further embodiments, the presence or effect of a gRNA molecule in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

Generally, lipid particles will not be delivered orally. However, in certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged gRNA molecule suspended in diluents such as water, saline, or PEG 400; (b) capsules, sachets, or tablets, each containing a predetermined amount of a gRNA molecule, as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a gRNA molecule in a flavor, e.g., sucrose, as well as pastilles comprising the therapeutic nucleic acid in an inert base, such as gelatin and glycerin or sucrose and acacia emulsions, gels, and the like containing, in addition to the gRNA molecule, carriers known in the art.

In another example of their use, lipid particles can be incorporated into a broad range of topical dosage forms. For instance, a suspension containing nucleic acid-lipid particles can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as gRNA associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of gRNA molecules to lipid, the particular gRNA used, the disease being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of gRNA molecules can be to any cell grown in culture. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 µmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 µg/ml, more preferably about 0.1 µg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of a nucleic acid-lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of the lipid particle based on their relative effect on binding/uptake or fusion with/destabilization of the endosomal membrane. This assay allows one to determine quantitatively how each component of the lipid particle affects delivery efficiency, thereby optimizing the lipid particle. Usually, an ERP assay measures expression of a reporter protein (e.g., luciferase, β-galactosidase, green fluorescent protein (GFP), etc.), and in some instances, a lipid particle formulation optimized for an expression plasmid will also be appropriate for encapsulating a gRNA. In other instances, an ERP assay can be adapted to measure downregulation of transcription or translation of a target sequence in the presence or absence of a gRNA. By comparing the ERPs for each of the various lipid particles, one can readily determine the optimized system, e.g., the lipid particle that has the greatest uptake in the cell.

C. Detection of Lipid Particles

In some embodiments, the lipid particles of the present invention are detectable in the subject at about 1, 2, 3, 4, 5, 6, 7, 8 or more hours. In other embodiments, the lipid particles of the present invention are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a gRNA sequence, detection of the target sequence of interest (i.e., by detecting expression or reduced expression of the sequence of interest), detection of a compound modulated by an EBOV protein (e.g., interferon), detection of viral load in the subject, or a combination thereof.

1. Detection of Particles

Lipid particles of the invention can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3H$, $^{125}I$, $^{35}S$, $^{14}C$, $^{32}P$, $^{33}P$, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., gRNA molecules) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., Short Protocols in Molecular Biology, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), C&EN 36; *The Journal Of NIH Research,* 3:81 (1991); Kwoh et al., *Proc. Natl. Acad. Sci. USA,* 86:1173 (1989); Guatelli et al., *Proc. Natl. Acad. Sci. USA,* 87:1874 (1990); Lomell et al., *J Clin. Chem.,* 35:1826 (1989); Landegren et al., *Science,* 241:1077 (1988); Van Brunt, *Biotechnology,* 8:291 (1990); Wu and Wallace, *Gene,* 4:560 (1989); Barringer et al., *Gene,* 89:117 (1990); and Sooknanan and Malek, *Biotechnology,* 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

This example describes CRISPR/Cas9-induced gene editing of an endogenous gene following delivery of messenger RNA (mRNA) and single guide RNA (gRNA) to a mouse liver in vivo via lipid nanoparticles (LNP).

Mice were injected intravenously with a LNP formulation of mRNA for the Cas9 protein (2 mg/kg body weight) and a LNP formulation of a gRNA (0.42 mg/kg) containing a target sequence within the mouse Pcsk9 gene. The gRNA contained the 20 base-pair target site GGCTGATGAGGCCGCACATG (SEQ ID NO:6), which lies within exon 1 of mouse Pcsk9.

Two days post-treatment, the animal livers were harvested and hepatic genomic DNA was isolated. This DNA isolate was used as a template for polymerase chain reaction to generate an amplicon of 415 base pairs in length containing the CRISPR target cut site 291 base pairs from the amplicon end. Surveyor assay (Guschin et al., *Methods Mol. Biol.*, 649, 247 (2010)) was run to detect small insertion/deletion (indel) mutations at the target cut site, and 100% (6/6) of treated animals showed a positive result for gene editing, while 0% (0/9) of the negative control animals (Saline-treated or LNP-mRNA only-treated) showed a positive result.

This positive Surveyor result from the harvested mouse livers provided evidence that LNP can be utilized to deliver Cas9 mRNA and gRNA to the liver in vivo and that the intended activity of the CRISPR reagents, i.e., target site-specific DNA cleavage followed by imprecise repair and mutagenesis, can be achieved.

Example 2

This example describes CRISPR/Cas9-induced gene editing of an exogenously introduced hepatitis B virus (HBV) genome following delivery of messenger RNA (mRNA) and single guide RNA (gRNA) to a mouse liver in vivo via lipid nanoparticles (LNP).

HBV DNA was delivered into the livers of NOD-SCID mice via hydrodynamic injection (HDI) in the tail vein with a 1.3-overlength HBV plasmid (10 µg/mouse in 1.6 mL saline in <5 sec). HBV plasmid HDI results in a stable pool of HBV DNA in the mouse liver and stable expression of HBV antigens.

Seven days post-HDI, the mice were injected intravenously with a LNP formulation of mRNA for the Cas9 protein (2 mg/kg body weight) and a LNP formulation of a gRNA (0.44 mg/kg) containing a target sequence within the HBV RT gene. The gRNA contained the 20 base-pair target site TTTCAGTTATATGGATGATG (SEQ ID NO:7), which lies in the HBV RT gene (Genbank ID: V01460; 2437-2456).

Two days post-treatment, the animal livers were harvested and hepatic DNA was isolated. This DNA isolate was used as a template for polymerase chain reaction to generate an amplicon of 562 base pairs in length containing the CRISPR target cut site 447 base pairs from the amplicon end. Surveyor assay (Guschin et al., *Methods Mol. Biol.*, 649, 247 (2010)) was run to detect small insertion/deletion (indel) mutations at the target cut site, and 100% (8/8) of treated animals showed a positive result for gene editing, while 0% (0/14) of the negative control animals (Saline-treated, LNP-mRNA only-treated, or entecavir-treated) showed a positive result.

This positive Surveyor result from the harvested mouse livers provided evidence that LNP can be utilized to deliver Cas9 mRNA and gRNA to the liver in vivo and that the intended activity of the CRISPR reagents, i.e., target site-specific DNA cleavage followed by imprecise repair and mutagenesis, can be achieved, specifically the targeting of exogenous HBV DNA.

What is claimed is:

1. A pharmaceutical composition comprising a first population of nucleic acid-lipid particles, wherein the nucleic acid-lipid particles of the first population comprise:

(a) one or more guide RNA (gRNA) sequences that comprise a first sequence that corresponds to a target sequence and a second sequence that is a tracer RNA sequence located 3' of the first sequence;

(b) a cationic lipid; and (c) a non-cationic lipid, which composition further comprises a pharmaceutically acceptable carrier, which composition also comprises a second population of nucleic acid-lipid particles that comprise a mRNA sequence encoding a Cas9, which second population of nucleic acid-lipid particles does not comprise the gRNA as described for the first population of nucleic acid-lipid particles.

2. The pharmaceutical composition of claim 1, wherein the mRNA sequence encoding the Cas9 further comprises a sequence encoding a nuclear localization signal (NLS).

3. The pharmaceutical composition of claim 1, wherein the mRNA sequence encoding the Cas9 further comprises a polyA tail, a 5' untranslated region (UTR) and/or a 3' UTR.

4. The pharmaceutical composition of claim 1, wherein the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA; Compound (15)), 3-((6Z,9Z,28Z,31Z)-heptatriaconta-6,9,28,31-tetraen-19-yloxy)-N,N-dimethylpropan-1-amine (DLin-MP-DMA; Compound (8)), (6Z,9Z,28Z,31Z)-heptatriaconta-6,9,28,31-tetraen-19-yl 4-(dimethylamino)butanoate) (Compound (7)), (6Z,16Z)-12-((Z)-dec-4-enyl)docosa-6,16-dien-11-yl 5-(dimethylamino)pentanoate (Compound (13)), a salt thereof, and a mixture thereof.

5. The pharmaceutical composition of claim 1, wherein the non-cationic lipid is cholesterol.

6. The pharmaceutical composition of claim 1, wherein the non-cationic lipid is a phospholipid.

7. The pharmaceutical composition of claim 1, wherein the first population and the second population of nucleic acid lipid particles each comprise a conjugated lipid that inhibits aggregation of particles.

8. The pharmaceutical composition of claim 7, wherein the conjugated lipid that inhibits aggregation of particles is a polyethyleneglycol (PEG)-lipid conjugate.

9. The pharmaceutical composition of claim 8, wherein the PEG-lipid conjugate is a PEG-DAA conjugate.

10. The pharmaceutical composition of claim 7, wherein the conjugated lipid that inhibits aggregation of particles comprises from about 0.5 mol % to about 3 mol % of the total lipid present in the particle.

11. The pharmaceutical composition of claim 1, wherein the gRNA is fully encapsulated in the particle.

12. The pharmaceutical composition of claim 1, wherein the particle has a total lipid:gRNA mass ratio of from about 5:1 to about 15:1.

13. The pharmaceutical composition of claim 1, wherein the particle has an electron dense core.

14. The pharmaceutical composition of claim 1, wherein the nucleic acid lipid particles of the first population comprise two different gRNA sequences.

15. A method for silencing expression of a target gene in a cell, the method comprising the step of contacting a cell comprising an expressed target gene with the composition of claim 1 under conditions to silence the expression of the gene within the cell so as to silence expression of the target gene.

* * * * *

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 1

Pro Lys Lys Lys Arg Lys Val
1               5

<210> SEQ ID NO 2
<211> LENGTH: 4140
<212> TYPE: DNA
<213> ORGANISM: Streptococcus pyogenes

<400> SEQUENCE: 2

| | | | | | |
|---|---|---|---|---|---|
| atggacaaga | agtactccat | tgggctcgat | atcggcacaa | acagcgtcgg | ctgggccgtc | 60 |
| attacgacg | agtacaaggt | gccgagcaaa | aaattcaaag | ttctgggcaa | taccgatcgc | 120 |
| cacagcataa | agaagaacct | cattggcgcc | ctcctgttcg | actccgggga | gacggccgaa | 180 |
| gccacgcggc | tcaaaagaac | agcacggcgc | agatataccc | gcagaaagaa | tcggatctgc | 240 |
| tacctgcagg | agatctttag | taatgagatg | gctaaggtgg | atgactcttt | cttccatagg | 300 |
| ctggaggagt | ccttttttggt | ggaggaggat | aaaaagcacg | agcgccaccc | aatctttggc | 360 |
| aatatcgtgg | acgaggtggc | gtaccatgaa | aagtacccaa | ccatatatca | tctgaggaag | 420 |
| aagcttgtag | acagtactga | taaggctgac | ttgcggttga | tctatctcgc | gctggcgcat | 480 |
| atgatcaaat | ttcggggaca | cttcctcatc | gagggggacc | tgaacccaga | caacagcgat | 540 |
| gtcgacaaac | tctttatcca | actggttcag | acttacaatc | agcttttcga | agagaacccg | 600 |
| atcaacgcat | ccggagttga | cgccaaagca | atcctgagcg | ctaggctgtc | caaatcccgg | 660 |
| cggctcgaaa | acctcatcgc | acagctccct | ggggagaaga | gaacggcct | gtttggtaat | 720 |
| cttatcgccc | tgtcactcgg | gctgaccccc | aactttaaat | ctaacttcga | cctggccgaa | 780 |
| gatgccaagc | ttcaactgag | caaagacacc | tacgatgatg | atctcgacaa | tctgctggcc | 840 |
| cagatcggcg | accagtacgc | agaccttttt | ttggcggcaa | agaacctgtc | agacgccatt | 900 |
| ctgctgagtg | atattctgcg | agtgaacacg | agatcacca | agctccgct | gagcgctagt | 960 |
| atgatcaagc | gctatgatga | gcaccaccaa | gacttgactt | tgctgaaggc | ccttgtcaga | 1020 |
| cagcaactgc | ctgagaagta | caaggaaatt | ttcttcgatc | agtctaaaaa | tggctacgcc | 1080 |
| ggatacattg | acggcggagc | aagccaggag | gaattttaca | aatttattaa | gcccatcttg | 1140 |
| gaaaaaatgg | acggcaccga | ggagctgctg | gtaaagctta | acagagaaga | tctgttgcgc | 1200 |
| aaacagcgca | ctttcgacaa | tggaagcatc | ccccaccaga | ttcacctggg | cgaactgcac | 1260 |
| gctatcctca | ggcggcaaga | ggatttctac | ccctttttga | agataacag | ggaaaagatt | 1320 |
| gagaaaatcc | tcacatttcg | gataccctac | tatgtaggcc | ccctcgcccg | gggaaattcc | 1380 |
| agattcgcgt | ggatgactcg | caaatcagaa | gagaccatca | ctccctggaa | cttcgaggaa | 1440 |
| gtcgtggata | aggggcctc | tgcccagtcc | ttcatcgaaa | ggatgactaa | ctttgataaa | 1500 |
| aatctgccta | acgaaaaggt | gcttcctaaa | cactctctgc | tgtacgagta | cttcacagtt | 1560 |
| tataacgagc | tcaccaaggt | caaatacgtc | acagaaggga | tgagaaagcc | agcattcctg | 1620 |
| tctggagagc | agaagaaagc | tatcgtggac | ctcctcttca | agacgaaccg | gaaagttacc | 1680 |
| gtgaaacagc | tcaaagaaga | ctatttcaaa | aagattgaat | gtttcgactc | tgttgaaatc | 1740 |
| agcggagtgg | aggatcgctt | caacgcatcc | ctgggaacgt | atcacgatct | cctgaaaatc | 1800 |
| attaaagaca | aggacttcct | ggacaatgag | gagaacgagg | acattcttga | ggacattgtc | 1860 |
| ctcacccctta | cgttgtttga | agataggag | atgattgaag | aacgcttgaa | aacttacgct | 1920 |

```
catctcttcg acgacaaagt catgaaacag ctcaagaggc gccgatatac aggatggggg    1980
cggctgtcaa gaaaactgat caatgggatc cgagacaaga gagtggaaa gacaatcctg    2040
gattttctta agtccgatgg atttgccaac cggaacttca tgcagttgat ccatgatgac   2100
tctctcacct ttaaggagga catccagaaa gcacaagttt ctggccaggg ggacagtctt    2160
cacgagcaca tcgctaatct tgcaggtagc ccagctatca aaaagggaat actgcagacc   2220
gttaaggtcg tggatgaact cgtcaaagta atgggaaggc ataagcccga gaatatcgtt   2280
atcgagatgg cccgagagaa ccaaactacc cagaagggac agaagaacag tagggaaagg   2340
atgaagagga ttgaagaggg tataaaagaa ctggggtccc aaatccttaa ggaacaccca   2400
gttgaaaaca cccagcttca gaatgagaag ctctacctgt actacctgca gaacggcagg   2460
gacatgtacg tggatcagga actggacatc aatcggctct ccgactacga cgtggatcat   2520
atcgtgcccc agtcttttct caaagatgat tctattgata taaagtgtt gacaagatcc    2580
gataaaaata gagggaagag tgataacgtc ccctcagaag aagttgtcaa gaaaatgaaa   2640
aattattggc ggcagctgct gaacgccaaa ctgatcacac aacggaagtt cgataatctg   2700
actaaggctg aacgaggtgg cctgtctgag ttggataaag ccggcttcat caaaaaggcag   2760
cttgttgaga cacgccagat caccaagcac gtggcccaaa ttctcgattc acgcatgaac   2820
accaagtacg atgaaaatga caaactgatt cgagaggtga agttattac tctgaagtct    2880
aagctggtct cagatttcag aaaggacttt cagttttata aggtgagaga gatcaacaat   2940
taccaccatg cgcatgatgc ctacctgaat gcagtggtag gcactgcact tatcaaaaaa   3000
tatcccaagc ttgaatctga atttgtttac ggagactata agtgtacga tgttaggaaa    3060
atgatcgcaa agtctgagca ggaaataggc aaggccaccg ctaagtactt cttttacagc    3120
aatattatga atttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta   3300
cagaccggag gcttctccaa ggaaagtatc ctcccgaaaa ggaacagcga caagctgatc   3360
gcacgcaaaa aagattggga ccccaagaaa tacgcggat tcgattctcc tacagtcgct    3420
tacagtgtac tggttgtggc caagtggag aaagggaagt ctaaaaaact caaaagcgtc    3480
aaggaactgc tgggcatcac aatcatggag cgatcaagct tcgaaaaaaa ccccatcgac   3540
tttctcgagg cgaaaggata taagaggtc aaaaaagacc tcatcattaa gcttcccaag    3600
tactctctct tgagcttga aaacggccgg aaacgaatgc tcgctagtgc gggcgagctg    3660
cagaaaggta acgagctggc actgccctct aaatacgtta atttcttgta tctggccagc   3720
cactatgaaa agctcaaagg gtctcccgaa gataatgagc agaagcagct gttcgtggaa    3780
caacacaaac actaccttga tgagatcatc gagcaaataa gcgaattctc caaaagagtg   3840
atcctcgccg acgctaacct cgataaggtg ctttctgctt acaataagca cagggataag   3900
cccatcaggg agcaggcaga aaacattatc cacttgttta ctctgaccaa cttgggcgcg   3960
cctgcagcct tcaagtactt cgacaccacc atagacagaa agcggtacac ctctacaaag    4020
gaggtcctgg acgccacact gattcatcag tcaattacgg ggctctatga aacaagaatc   4080
gacctctctc agctcggtgg agacagcagg gctgacccca agaagaagag gaaggtgtga   4140
```

<210> SEQ ID NO 3
<211> LENGTH: 100
<212> TYPE: RNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 3
nnnnnnnnnn nnnnnnnnnn guuuuagagc uagaaauagc aaguuaaaau aaggcuaguc        60
cguuaucaac uugaaaaagu ggcaccgagu cggugcuuuu                             100

<210> SEQ ID NO 4
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
guuuuaguac ucuggaaaca gaaucuacua aaacaaggca aaaugccgug uuuaucucgu        60
caacuuguug gcgagauuuu                                                   80

<210> SEQ ID NO 5
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
guuuuuguac ucgaaagaag cuacaaagau aaggcuucau gccgaaauca acacccuguc        60
auuuuauggc agguguuuu                                                    80

<210> SEQ ID NO 6
<211> LENGTH: 20
<212> TYPE: DNA
<213> ORGANISM: Mus sp.

<400> SEQUENCE: 6
ggctgatgag gccgcacatg                                                   20

<210> SEQ ID NO 7
<211> LENGTH: 20
<212> TYPE: DNA
<213> ORGANISM: Hepatitis B virus

<400> SEQUENCE: 7
tttcagttat atggatgatg                                                   20
```